United States Patent
Rolland et al.

(10) Patent No.: US 6,514,947 B2
(45) Date of Patent: *Feb. 4, 2003

(54) FORMULATED NUCLEIC ACID COMPOSITIONS AND METHODS OF ADMINISTERING THE SAME FOR GENE THERAPY

(75) Inventors: Allain Rolland, The Woodlands, TX (US); Russell J. Mumper, The Woodlands, TX (US)

(73) Assignee: Valentis, Inc., Burlingame, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/798,974

(22) Filed: Feb. 11, 1997

(65) Prior Publication Data

US 2002/0103142 A1 Aug. 1, 2002

Related U.S. Application Data

(63) Continuation-in-part of application No. 08/372,213, filed on Jan. 13, 1995, now Pat. No. 6,040,295.

(51) Int. Cl.[7] ............ A01N 43/04; A61K 9/24; A61K 9/16; A61K 9/50
(52) U.S. Cl. ............ 514/44; 424/472; 424/497
(58) Field of Search ............ 514/44; 424/472, 424/497

(56) References Cited

U.S. PATENT DOCUMENTS

| | | | |
|---|---|---|---|
| 5,292,516 A | 3/1994 | Viegas et al. | 424/423 |
| 5,470,568 A | 11/1995 | Lee | 424/78.02 |
| 5,512,436 A | 4/1996 | Stone | 435/6 |
| 5,531,925 A | 7/1996 | Landh | 252/299.01 |
| 5,552,309 A | 9/1996 | March | 435/172.3 |
| 5,573,934 A | 11/1996 | Hubbell et al. | 435/177 |
| 5,578,325 A | 11/1996 | Domb et al. | 424/501 |
| 5,580,575 A | 12/1996 | Unger et al. | 424/450 |
| 5,583,034 A | 12/1996 | Green et al. | 435/240.2 |
| 5,591,721 A | 1/1997 | Agrawal et al. | 514/44 |
| 5,593,974 A | 1/1997 | Rosenberg et al. | 514/44 |
| 5,656,611 A | 8/1997 | Kabanov et al. | 514/44 |
| 5,770,580 A | 6/1998 | Ledley et al. | 514/44 |
| 5,797,870 A | 8/1998 | March et al. | 604/49 |
| 5,817,321 A | 10/1998 | Alakhov et al. | 424/400 |

FOREIGN PATENT DOCUMENTS

| | | |
|---|---|---|
| WO | 9011092 | 10/1990 |
| WO | 9424983 | 11/1994 |
| WO | WO 95/10265 | 4/1995 |
| WO | 9524929 | 9/1995 |
| WO | 9639124 | 12/1996 |

OTHER PUBLICATIONS

C. Koller and P. Buri, "Propriétés et intérêt pharmaceuticique des gels thermoréversibles àbase de poloxamers et poloxamines." S.T.P. Pharma 3(2): 115–124, 1987.

Kabanov, et al. "A new class of drug carriers: micelles of poly(oxyethylene)–poly(oxypropylene) block copolymers as microcontainers for drug targeting from blood in brain" J. Controlled Release 22 (1992) 141–158.

Simons et al. "Antisense c–myb oligonucleotides inhibit intimal arterial smooth muscle cell accumulation in vivo" Nature 359, 67–70 (1992).

(List continued on next page.)

Primary Examiner—Jezia Riley
(74) Attorney, Agent, or Firm—Michael J. Wise

(57) ABSTRACT

Compositions and methods for administering nucleic acid compositions in vitro to cells in culture or in vivo to an organism whereby the uptake of nucleic acids is enhanced are provided. Various compositions, including those incorporating protective, interactive, non-condensing compounds, are utilized to protect and administered nucleic acid formulation, thereby prolonging the localized bioavailability of the administered nucleic acid and enhancing expression from the nucleic acid.

20 Claims, 8 Drawing Sheets

OTHER PUBLICATIONS

Klang et al. "Physiochemical characterization and acute toxicity evaluation of a positively–charged submicron emulsion vehicle" J. Pharm. Pharmacol. 46:986–993 (1994).

Curier, D.T. et al. "High Efficiency Gene Transfer Mediated by Adenovirus Coupled to DNA Polylysme Complexes", Human Gene Therapy, vol. 3, pp. 147–154, 1992.

Datta, S. K. et al. "Herbicide–resistant Indica rice plants from IRRI breeding line IR72 after PEG–mediated transformation of protoplasts", Plant Molecular Biology, vol. 20, pp. 619–629, 1992.

Drobnitz, J. "Biodegradable soluble macromolecules as drug carriers", Advanced Drug Delivery Reviews, vol. 3, 229–245, 1989.

Haensler, J. et al. "Polyamidoamine Cascade Polymers Mediate Efficient Transfection of Cells in Culture", Bioconjugate Chemistry, vol. 4, pp. 372–379, 1993.

Kamath, K. R. et al. "Biodegradable hydrogels in drug delivery", Advanced Drug Delivery Reviews, vol. 11, pp. 59–84, 1993.

Kuo, P. Y. P.et al. "Novel Systems for Controlled Delivery of Macromolecules", Critical Reviews in Eukaryotic Gene Expression, vol. 6, No. 1, pp. 59–73, 1996.

Acsadi et al., "Human Dystrophin Expression in mdx Mice After Intramuscular Injection of DNA Constructs," *Nature* 352:815–818 (1991).

Akiyama et al., *Acta Neuropathol,* 83:584–589 (1992).

Alila et al., "Expression of biologically active human insulin–like growth factor–I following intramuscular injection of a formulated DNA plasmid in rats," *Human Gene Therapy* (1997).

Anderson et al., "Potocytosis: Sequestration and Transport of Small Molecules by Caveolae," *Science* 255:410–411 (1992).

Anwer et al., "Systemic effect of human growth hormone after intramuscular injection of a single dose of a muscle–specific gene medicine," *Nature Medicine* (1997).

Bennett et al., "Inhibition of Vascular Smooth Muscle Cell Proliferation in Vitro and in Vivo by c–myc Antisense Oligodeoxynucleotides," *J. Clin. Invest.* 93(2):820–828 (1994).

Benoit et al., *J. Anat.* 107:547–556 (1970).

Biswas et al., "Transgenic Indica rice (*Oryza sativa* L.) plants obtained by direct gene transfer to protoplasts," *Journal of Biotechnology* 32:1–10 (1994).

Carlson et al., *J. Orthopaedic Research* 8:485–494 (1990).

Caroni and Grandes, *Journal of Cell Biology* 110:1307–1317 (1990).

Caso et al., "Transfection in Micromonospora," *Appl. Environ. Microbiol.* 53(10):2544–47 (1987).

Coleman et al., "Non–viral IGF–I gene therapy reduces atrophy and loss of muscle strength in tibialis anterior muscles of hindlimb suspended mice," *American J. Phys.* (1997).

Chemla et al., "Effects of Antisense Oligonucleotides on Myointimale Hyperplasia in a Model of Abdominal Aortic Trauma in the Rat," *Archives des Maladies Due Coeur Et Des Vaisseaux* 88(3):381–389 (1995).

Coney et al., "Facilitated DNA inoculation induces anti–HIV–1 immunity in vivo," *Vaccine* 12:1545–50 (1994).

Corr et al., *J. Exp. Med.* 184:1555–1560 (1996).

Current Protocols in Molecular Biology, Chapter 9, Unit 9.6A Reporter System Using Chloramphenicol Acetyltransferase (1993).

Dahler et al., "Expression vectors encoding human growth hormone (hGH) controlled by human muscle–specific promoters: prospects for regulated production of hGH delivered by myoblast transfer or intravenous injection," *Gene* 145:305–310 (1994).

Danko et al., "Pharmacological enhancement of in vivo foreign gene expression in muscle," *Gene Therapy* 1:114–121 (1994).

Davis et al., "Direct gene transfer into skeletal muscle in vivo: factors affecting efficiency of transfer and stability of expression," *Human Gene Therapy* 4:151–159 (1993).

Davis et al., "Direct gene transfer in skeletal muscle: plasmid DNA–based immunization against the hepatitis B virus surface antigen," *Vaccine* 12:1503–1509 (1994).

Davis et al., "DNA–based immunization for hepatitis B induces continuous secretion of antigen and high levels of circulating antibody," *Human Molec. Genet.* 2:1847–1851 (1993).

Davis et al., DNA vaccine for hepatitis B: evidence for immunogenicity in chimpanzees and comparison with other vaccines, *Proc. Natl. Acad. Sci. USA* 93:7213–7218 (1996).

Davis et al., "Plasmid DNA is superior to viral vectors for direct gene transfer into adult mouse skeletal muscle," *Human Gene Therapy* 4:733–40 (1993).

Doe et al., *Proc. Natl. Acad. Sci. USA* 93:8578–8583 (1996).

Donnelly et al., *J. Immunol. Meth.* 176:145–152 (1994).

Donnelly et al., "Preclinical efficacy of a prototype DNA vaccine: enhanced protection against antigenic drift in influenza virus," *Nature Medicine* 1:521–2 (1995).

Dowty et al., *Proc. Natl. Acad. Sci. USA* 92:4572–4576 (1995).

Dowty and Wolff, "Possible mechanisms of DNA uptake in skeletal muscle," in *Gene Therapeutics: Methods and Applications of Direct Gene Transfer*, edited by J.A. Wolff, Birkhauser, Boston, pp. 82–98 (1994).

Duncan, "Drug–polymer conjugates: potential for Improved chemotherapy," *Anti–Cancer Drugs* 3:175–210 (1992).

Edelman et al., "c–myc in vasculoproliferative disease," *Circulation Research* 76(2):176–182 (1995).

Ewel et al., "Polyinosinic–Polycytidylic Acid Complexed with Poly–L–lysine and Carboxymethylcellulose in Combination with Interleukin 2 in Patients with Cancer: Clinical and Immunological Effects," *Cancer Research* 52:3005–3010 (1992).

Fazio et al., "Accumulation of human apolipoprotein–E in rat plasma after in vivo intramuscular injection of naked DNA," *Biochemical and Biophysical Research Communications* 200:298–305 (1994).

Felgner et al., "Lipofection: A Highly Efficient, Lipid–mediated DNA–transfection Procedure," *Proc. Natl. Acad. Sci. USA* 84:7413–7417 (1987).

Fraley et al., "Introduction of Liposome Encapsulated SV40 DNA into Cells," *J. Biol. Chem.* 225(21):10431–10435 (1980).

Fulton et al., "Luminescent Reporter Gene Assays for Luciferase and β–galactosidase Using a Liquid Scintillation Counter," *BioTechniques* 14(5):762–763 (1993).

Galaev et al., *J. Chrom. A.* 684:45–54 (1994).

Ghiasi et al., "Vaccination of mice with herpes simplex virus type 1 glycoprotein D DNA produces low levels of protection against lethal HSV–1 challenge," *Antiviral Research* 28:147–57 (1995).

Haensler and Szoka, "Polyamidoamine Cascade Polymers Mediate Efficient Transfection of Cells in Culture," *Bioconjugate Chem.* 4:372–379 (1993).

Hagstrom et al., *Biochem. Mol. Med.* 58:113–121 (1996).

Haida et al., *Exper. Neuro.* 103:68–76 (1989).

Hall–Craggs, *Br. J. Exp. Pathol,* 61:139–149 (1980).

Hoffman et al., "Nucleic acid malaria vaccines. Current status and potential," *Ann. N.Y. Acad. Sci.* 772:88–94 (1995).

*Human Gene Therapy* 3:147–154 (1992), Curiel et al.

Hung et al., "Suppression of intra–articular responses to interleukin–1 by transfer of the interleukin–1 receptor antagonist gene by synovium," *Gene Therapy* 1:64–69 (1994).

Ishii et al., *Int. J. Neurosci.* 26:109–127 (1985).

Jain and Magrath, "A Chemiluminescent Assay for Quantitation of β–Galactosidase in the Femtogram Range: Application to Quantitation of β–Galactosidase in lacZ–Transfected Cells," *Analytical Biochemistry* 199:119–124 (1991).

Jiao et al., "Direct Gene Transfer into Nonhuman Primate Myofibers In Vivo," *Human Gene Therapy* 3:21–33 (1992).

Kabanov and Kabanov, *Bioconj. Chem.* 6:7–20 (1995).

Kabanov et al., "DNA Interpolyelectroylte Complexes as a Tool for Efficient Cell Transformation," *Biopolymers* 31:1437–1443 (1991).

Kamath and Park, "Biodegradable hydrogels in drug delivery," *Advanced Drug Delivery Reviews* 11:59–84 (1993).

Karpati and Acsadi, "The potential for gene therapy in Duchenne Muscular Dystrophy and other genetic muscle diseases," *Muscle Nerve* 16:1141–53 (1993).

Klebe et al., "Uptake by Cells of Nucleic Acids Promoted by Compounds Sharing the Pleiotropic Effects of Poly(Ethylene Glycol)," *Teratogenesis, Carcinogenesis and Mutagenesis* 6(3):245–250 (1986).

Kriesel et al., "Nucleic acid vaccine encoding gD2 protects mice from herpes simplex virus type 2 disease," *J. Inf. Dis.* 173:536–541 (1996).

Kumar and Sercarz, *Nature Medicine* 2:857–859 (1996).

Kuo et al., "Novel Systems for Controlled Delivery of Macromolecules," *Critical Reviews in Eukaryotic Gene Expression* 6(1):59–73 (1996).

Kuwahara–Rundell et al., "Expression of dog Factor–IX protein after intramuscular DNA injections in mice," *J. Cell. Biochem.* Suppl. 18A:233 (1994).

Lagging et al., "Immune response to plasmid DNA encoding the hepatitis C virus core protein," *Journal of Virology* 69:5859–63 (1995).

Lai et al., "Protection against Mycoplasma pulmonis infection by genetic vaccination," *DNA Cell Biol.* 14:643–51 (1995).

Ledley, "Nonviral Gene Therapy: The Promise of Genes as Pharmaceutical Products," *Human Gene Therapy* 6:1129–1144 (1995).

Levy et al., "Characterization of plasmid DNA transfer into mouse skeletal muscle: evaluation of uptake mechanism, expression and secretion of gene products into blood," *Gene Therapy* 3:201–211 (1996).

Liu, et al.(Eds.), *DNA Vaccines: A new era in vaccinology,* vol. 772, *Ann. NY. Acad. Sci.,* New York (1995).

Lopez–Macias et al., "Induction of antibodies against Salmonella typhi OmpC porin by naked DNA immunization," *Ann. N.Y. Acad. Sci.* 772:285–288 (1995).

Lowrie et al., "Towards a DNA vaccine against tuberculosis," *Vaccine* 12:1537–1540 (1994).

Ma et al., "Intramuscular delivery of rat kallikrein–binding protein gene reverses hypotension in transgenic mice expressing human tissue kallikrein," *J. Biol. Chem.* 270:451–455 (1995).

Major et al., "DNA–based immunizaiton with chimeric vectors for the induction of immune responses against the hepatitis C virus nucleocapsid," *Journal of Virology* 69:5798–5805 (1995).

Manickan et al., "Genetic immunization against herpes simplex virus: Protection is mediated by CD4+ T lymphocytes," *J. Immunology* 155:259–265 (1995).

Manthorpe et al., "Gene therapy by intramuscular injection of plasmid DNA: studies on firely luciferase gene expression in mice," *Human Gene Therapy* 4:419–431 (1993).

March et al., *Human Gene Therapy* 6:41–53 (1995).

March et al., "Facilitation of Adenoviral Gene Delivery by Poloxamer 407," *Proceed. Intern. Symp. Control. Rel. Bioact. Mater.* 21 (1994).

McClements et al., "Immunization with DNA vaccines encoding glycoprotein D or glycoprotein B, alone or in combination, induces protective immunity in animal models of herpes simplex virus–2 disease," *Proc. Natl. Acad. Sci. USA* 93:11414–11420 (1996).

Miller et al., "Gene therapy by and for muscle cells," *Trends Genet.* 11:163–65 (1995).

Miller et al., "Expression of Factor–VII in vitro and in vivo following direct gene transfer into muscle: a model for hemophilia," *Gene Ther.* 1, Suppl.2, S16 (1994).

Monsigny et al., "Glycoconjugates as carriers for specific delivery of therapeutic drugs and genes," *Advanced Drug Delivery Reviews* 14:1–24 (1994).

Mumper et al., "Interactive polymeric gene delivery systems for enhanced muscle expression," *Pharmaceutical Research* 12(9):S80 at abstract 2005 (1995).

Mumper et al., "Polyvinyl derivatives for controlled gene delivery to muscle," *Pharmaceutical Research* 13(5):701–709 (1996).

Mumper et al., Protective Interactive Non–Condensing (PINC) Polymers for Enhance Plasmid Distribution and Expression in Rat Skeletal Muscle, *Gene Therapy* (1997).

Naffakh et al., *Human Gene Therapy* 7:11–21 (1994).

Neff et al., *J. Neurobiology* 24:1578–1588 (1993).

Nguyen et al., "Firefly Luciferase Luminescence Assays Using Scintillation Counters for Quantitation in Tansfected Mammalian Cells," *Analytical Biochemistry* 171:404–408 (1988).

Pande et al., "Direct DNA immunizaiton of mice with plasmid DNA encoding the tegument protein pp65(ppUL83) of human cytomegalovirus induces high levels of circulating antibody to the encoded protein," *Scand. J. Infect. Dis.* Suppl. 99:117–120 (1995).

Papisov, "Modeling in vivo transfer of long–circulating polymers (two classes of long circulating polymers and factors affecting their transfer n vivo)," *Advances Drug Delivery Reviews* 16:127–139 (1995).

Petrak, "Ch. 10—Design and Properties of Particulate Carriers for Intravascular Administration," in *Intravascular Particulate Carriers,* pp. 275–293 (1993).

Phillpotts et al., "Immunization with DNA polynucleotides protects mice against lethal challenge with St. Louis encephalitis virus," *Arch. Virol.* 141:743–49 (1996).

Rabinovsky et al., "Non–viral gene therapy enhances recovery following sciatic nerve crush," *Nature Medicine* (1997).

Raz et al., "Systemic immunological effects of cytokine genes injected into skeletal muscle," *Proc. Natl. Acad. Sci. USA* 90:4523–4527 (1993).

Russell et al., "Plasmid vaccination to elicit anti–idiotypic immune responses against surface immunoglobulin–positive B–cell malignancies," *Br. J. Haematol*, 86, Suppl. 1, 74 (1994).

Sedegah et al., "Protection against malaria by immunization with circumsporozoite protein plasmid DNA," *Proc. Natl. Acad. Sci. USA* 91:9866–9870 (1994).

Shaper et al., "A 796–base pair genomic region containing two cAMP–responsive elements (CRE)–like elements, mediates expression in transgenic mice," *J. Biol. Chem.* 269:25165–25171 (1994).

Shiver et al., "Cytotoxic T lymphocyte and helper T cell responses following HIV polynucleotide vaccination," *Ann. N.Y. Acad. Sci.* 772:198–208 (1995).

Sjoberg and Kanje, *Brain Research* 485:102–108 (1989).

Tarantino et al., *J. Pharm. Sci.* 83:1213–1216 (1994).

Tascon et al., "Vaccination against tuberculosis by DNA injection," *Nat. Med.* 2:888–892 (1996).

Tripathy et al., "Long–term expression of erythropoietin in the systemic circulation of mice after intramuscular injection of a plasmid DNA vector," *Proc. Natl. Acad. Sci. USA* 93:10876–10880 (19.

Uglea and Dumitriu–Medvichi, "Medical Applications of Synthetic Oligomers," in *Polymeric Biomaterials*, edited by Severian Dumitriu, Marcel Dekker, Inc. (1993).

Ulmer et al., *Current Opinion in Immunology* 8:531–536.

Ulmer et al., *Immunology* (1996).

Ulmer et al., "Protective immunity by intramuscular injection of low doses of influenza DNA vaccines," *Vaccine* 12:1541–1544 (1994).

Ulmer et al., "Heterologous protection against influenza by injection of DNA encoding a viral protein," *Science* 259:1745–1749 (1993).

Ulmer et al., Ann. NY. Acad. Sci., New York vol. 772.

Vitadello et al., "Gene transfer in regenerating muscle," *Human Gene Therapy* 5:11–18 (1994).

Wagner et al., "Transferrin–polycation Conjugates as Carriers for DNA Uptake Into Cells," *Proc. Natl. Acad. Sci. USA* 87:3410–3414 (1990).

Wang et al., "Gene inoculation generates immune responses against human immunodeficiency virus type 1," *Proc. Natl. Acad. Sci. USA* 90:4156–4160 (1993).

Weith et al., "Synthesis of cellulose derivatives containing the dihydropxyboryl group and a study of their capacity to form specific complexes with sugars and nucleic acid components," *Biochemistry* 9(22):4396–4401 (1970).

Wells and Goldspink, "Age and sex influence expression of plasmid DNA directly injected into mouse skeletal muscle," *FEBS Letters* 306:203–205 (1992).

Wells, "Improved gene transfer by direct plasmid injection associated with regeneration in mouse skeletal muscle," *FEBS Letters* 332:179–82 (1993).

Winegar et al., *Human Gene Therapy* 7:2185–2194.

Wolff et al., "Conditions Affecting Direct Gene Transfer into Rodent Muscle In Vivo," *BioTechniques* 11:474–485 (1991).

Wolff et al., "Direct Gene Transfer into Mouse Muscle In Vivo," *Science* 247:1465–1468 (1990).

Wolff et al., "Expression of Naked Plasmids by Cultured Myotubes and Entry of Plasmids into T Tubules and Caveolae of Mammalian Skeletal Muscle," *Journal of Cell Science* 103:1249–1259 (1992).

Wolff et al., *Hum. Mol. Genet.* 1:363–369 (1996).

Xiang et al., "Immune response to nucleic acid vaccines to rabies virus," *Virology* 209:569–579 (1995).

Xiong et al., "Muscle delivery of human kallikrein gene reduces blood pressure in hypertensive rats," *Hypertension* 25:715–719 (1995).

Yaroslavov et al., *FEBS Letters* 384:177–180 (1996).

Young et al., "Selective Inactivation of Eukaryotic β–Galactosidase in Assays for Inhibitors of HIV–1 TAT Using Bacterial β–Galactosidase as a Reporter Enzyme," *Anal. Biochem.* 215:24–30 (1993).

Zia et al., *Pharm. Res.* 8:502–504 (1991).

"Reporter System Using Chloramphenicol Acetyltransferase," in *Current Protocols in Molecular Biology*, Supplement 29, Chapter 9, Unit 9.6A, pp. 9.6.5–9.6.6 (1993).

Curiel et al., "High–Efficiency Gene Transfer Mediated by Adenovirus Coupled to DNA–Polylysine Complexes," *Human Gene Therapy* 3:147–154 (1992).

Miller and Boyce, "Gene therapy by an for muscle cells," *Trends in Genetics* 11:163–165 (1995).

Ulmer et al., "DNA vaccines," *Current Opinion in Immunology* 8:531–536 (1996).

Wolff et al., "Long–term persistence of plasmid DNA and foreign gene expression in mouse muscle," *Human Molecular Genetics* 1(6):363–369 (1992).

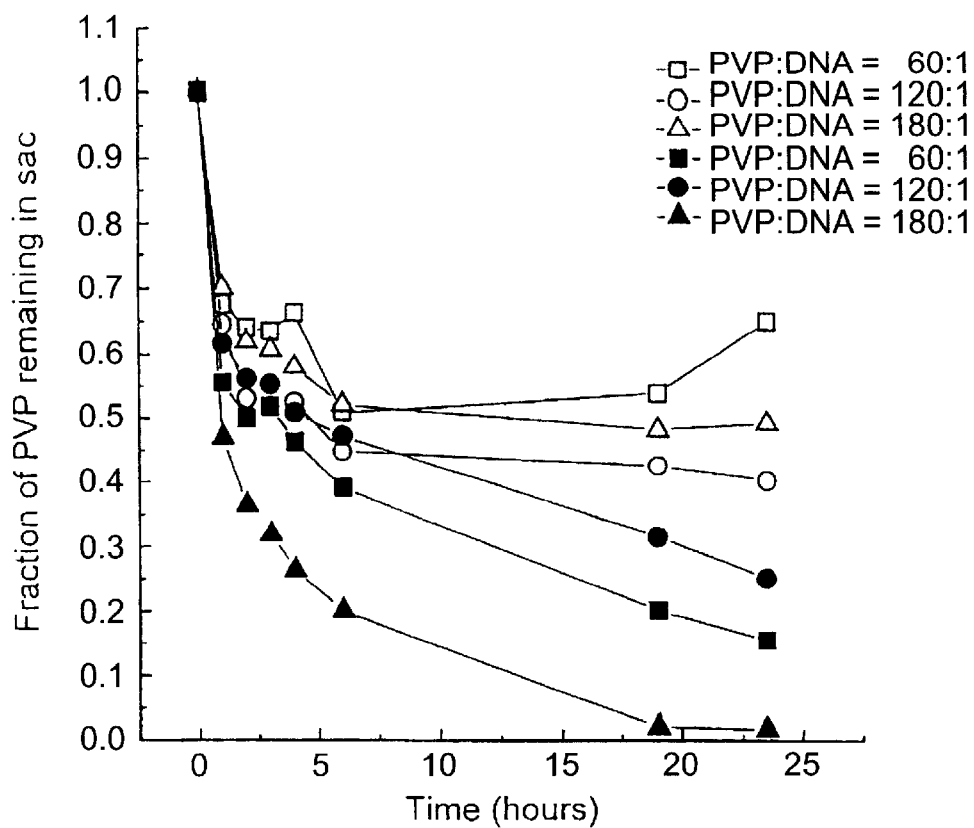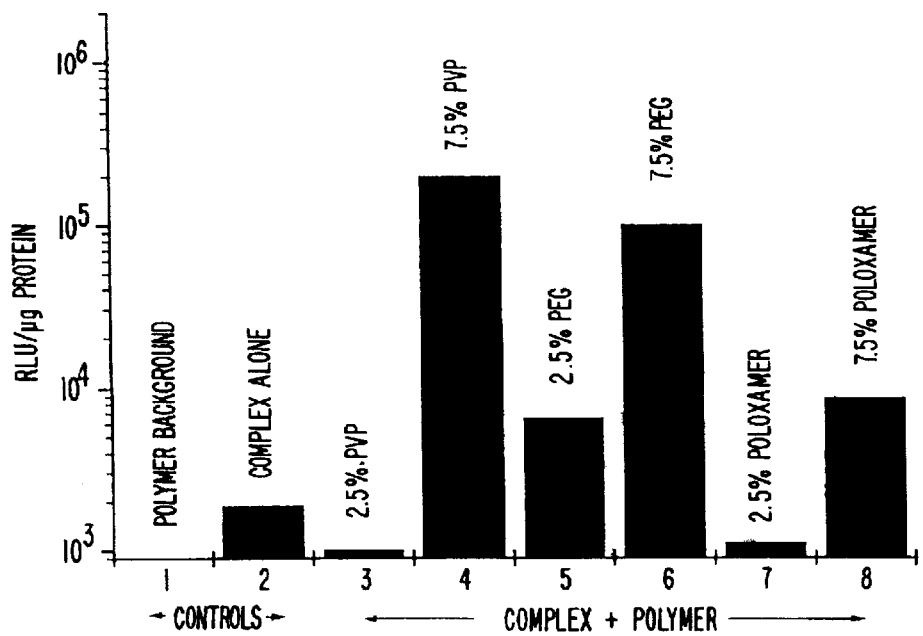

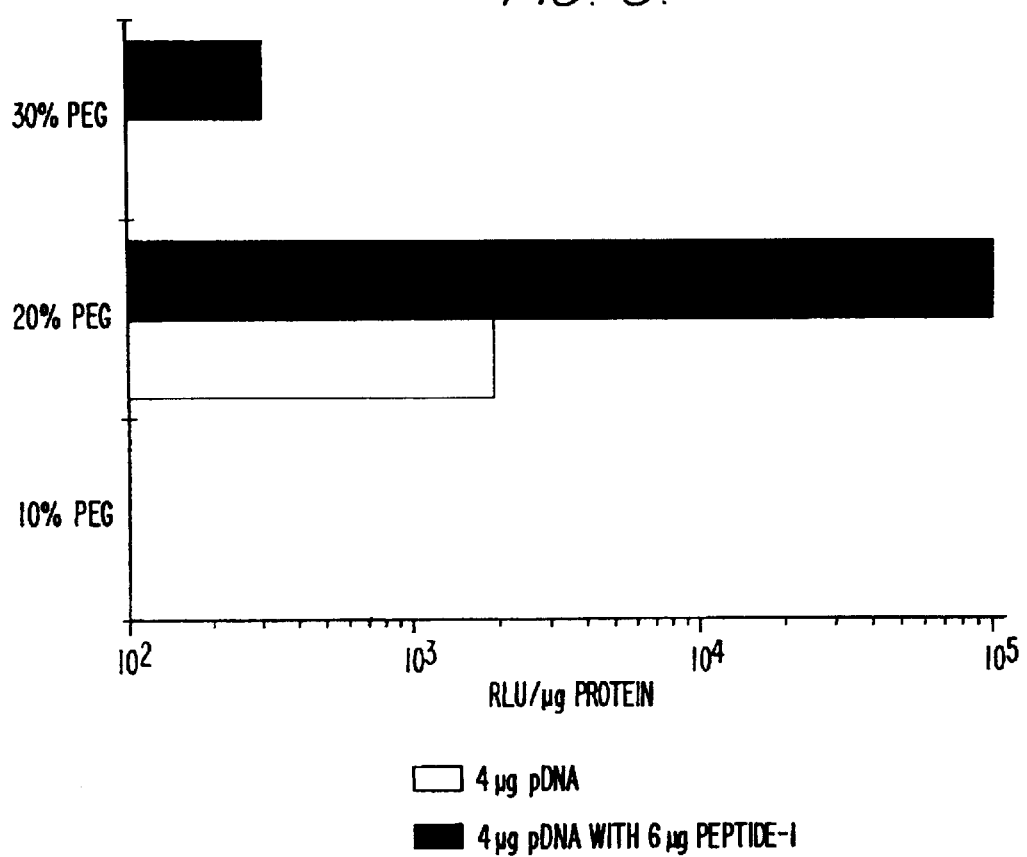

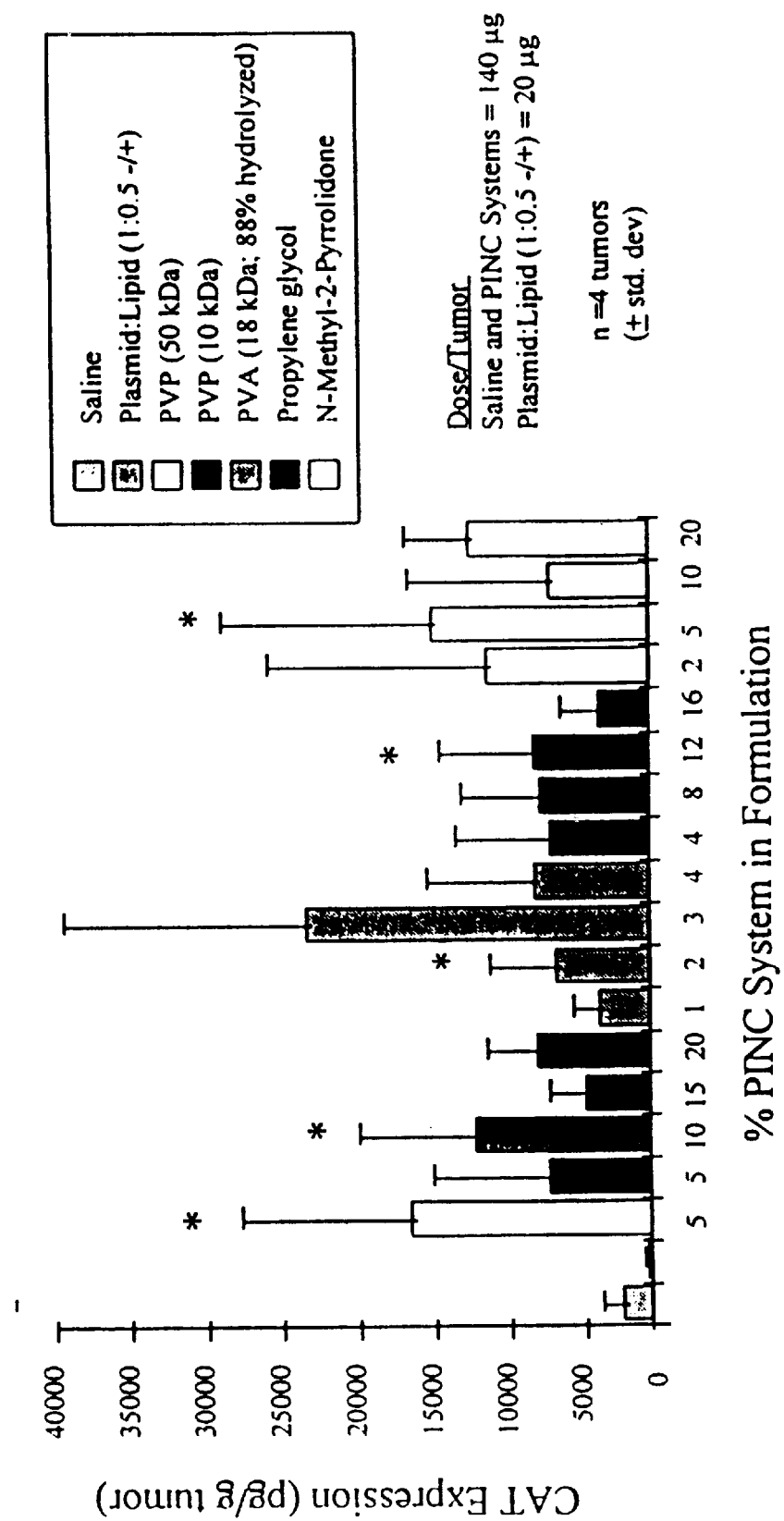

FORMULATED NUCLEIC ACID COMPOSITIONS AND METHODS OF ADMINISTERING THE SAME FOR GENE THERAPY

RELATED APPLICATION

This application is a continuation-in-part of Rolland et al., FORMULATED NUCLEIC ACID COMPOSITIONS AND METHODS OF ADMINISTERING THE SAME FOR GENE THERAPY, U.S. application Ser. No. 08/372,213, filed Jan. 13, 1995, now U.S. Pat. No. 6,040,295, which is incorporated herein by reference in its entirety, including drawings.

BACKGROUND OF THE INVENTION

The following information is presented solely to assist the understanding of the reader, none of the information is admitted to describe prior art to the claims of the present invention.

This invention relates to compositions and methods for the introduction of a formulated nucleic acid into a cell for the expression of a peptide or polypeptide. It is useful for in vitro transfections and in vivo for gene therapy, for among other things administration of therapeutic proteins, polypeptides and peptides and for vaccination.

Non-viral administration of nucleic acid in vivo has been accomplished by a variety of methods. These include lipofectin/liposome fusion: *Proc. Natl. Acad. Sci.*, Volume 84, pp. 7413–7417 (1993); polylysine condensation with and without adenovirus enhancement: *Human Gene Therapy*, Volume 3, pp. 147–154 (1992); and transferrin: transferrin receptor delivery of nucleic acid to cells: *Proc. Natl. Acad. Sci.*, Volume 87, pp. 3410–3414 (1990). The use of a specific composition consisting of polyacrylic acid has been disclosed in WO 94/24983. Naked DNA has been administered as disclosed in WO 90/11092.

An important goal of gene therapy, as an initial step in the process of ultimately obtaining expression of a product encoded by a nucleic acid, is to effect the uptake of nucleic acid by cells. Uptake of nucleic acid by cells is dependent on a number of factors, one of which is the length of time during which a nucleic acid is in proximity to a cellular surface. For instance, after intramuscular (i.m.) administration of plasmid DNA in buffer, a marked reduction in gene expression is observed if the muscle is massaged, presumably due to DNA leakage out of the muscle either directly or via lymphatic vessels (*Human Gene Therapy* 4:151–159; 1993). Accordingly, it would be desirable to formulate nucleic acids with compounds which would retard the rate at which nucleic acids diffuse or are carried away from a site at which cellular uptake of the nucleic acid is desired. Further, these compounds would be suitable for administration to an organism by means such as injection while maintaining or regaining the physical characteristics necessary to increase cellular uptake of nucleic acids.

SUMMARY OF THE INVENTION

This invention features compositions and methods for enhancing the administration to and uptake of nucleic acids by an organism. An efficient strategy for enhancing nucleic acid delivery in vivo is to protect the nucleic acid from degradation, thereby maintaining the administered nucleic acid at the target site in order to further increase its cellular uptake. Also, for in vitro administration, increasing the effective concentration of the nucleic acid at the cell surface should increase the efficiency of transfection. The compositions of the present invention which are used to administer nucleic acid comprise a compound which protects the nucleic acid and/or prolongs the localized bioavailability of the nucleic acid when administered to an organism in vivo, or in vitro in cell culture.

In connection with the compounds and compositions of this invention, the term "protects" or "protective" refers to an effect of the interaction between such a compound and a nucleic acid such that the rate of degradation of the nucleic acid is decreased in a particular environment. Such degradation may be due to a variety of different factors, which specifically include the enzymatic action of a nuclease. The protective action may be provided in different ways, for example, by exclusion of the nuclease molecules or by exclusion of water.

By "prolong the localized bioavailability of a nucleic acid" is meant that a nucleic acid when administered to an organism in a composition comprising such a compound will be available for uptake by cells for a longer period of time than if administered in a composition without such a compound, for example when administered in a formulation such as a saline solution. This increased availability of nucleic acid to cells could occur, for example, due to increased duration of contact between the composition containing the nucleic acid and a cell or due to protection of the nucleic acid from attack by nucleases. The compounds which prolong the localized bioavailability of a nucleic acid are suitable for internal administration.

By "suitable for internal administration" is meant that the compounds are suitable to be administered within the tissue of an organism, for example within a muscle or within a joint space, intradermally or subcutaneously. Other forms of administration which may be utilized are topical, oral, pulmonary, nasal and mucosal; for example, buccal, vaginal or rectal. Properties making a compound suitable for internal administration can include, for example, the absence of a high level of toxicity to the organism as a whole.

By "nucleic acid" is meant both RNA and DNA including: cDNA, genomic DNA, plasmid DNA or condensed nucleic acid, nucleic acid formulated with cationic lipids, nucleic acid formulated with peptides, cationic polymers, RNA or mRNA. In a preferred embodiment, the nucleic acid administered is plasmid DNA which comprises a "vector".

A "vector" is a nucleic acid molecule incorporating sequences encoding therapeutic product(s) as well as, various regulatory elements for transcription, translation, transcript stability, replication, and other functions as are known in the art.

A "transcript stabilizer" is a sequence within the vector which contributes to prolonging the half life (slowing the elimination) of a transcript.

"Post-translational processing" means modifications made to the expressed gene product. These may include addition of side chains such as carbohydrates, lipids, inorganic or organic compounds, the cleavage of targeting signals or propeptide elements, as well as the positioning of the gene product in a particular compartment of the cell such as the mitochondria, nucleus, or membranes. The vector may comprise one or more genes in a linear or circularized configuration. The vector may also comprise a plasmid backbone or other elements involved in the production, manufacture, or analysis of a gene product.

An "expression vector" is a vector which allows for production of a product encoded for by a nucleic acid sequence contained in the vector. For example, expression of a particular growth factor protein encoded by a particular gene.

A "DNA vector" is a vector whose native form is a DNA molecule. A "viral vector" is a vector whose native form is as the genomic material of a viral particle.

A "gene product" means products encoded by the vector. Examples of gene products include mRNA templates for translation, ribozymes, antisense RNA, proteins, glycoproteins, lipoproteins and phosphoproteins. The nucleic acid may be associated with a targeting ligand to effect targeted delivery.

A "targeting ligand" is a component of the carrier or vehicle or a moiety (a molecule or group) attached to a protective, interactive, non-condensing compound which binds to receptors, with an affinity for the ligand, on the surface or within compartments of a cell for the purpose of enhancing uptake or intracellular trafficking of the vector. Galactosyl residues, e.g., Tris-galactosyl residues, carnitine derivatives, mannosyl residues, e.g., mannose-6-phosphate, monoclonal and polyclonal antibodies, peptide ligands, and DNA-binding proteins represent non-limiting examples of targeting ligands which can be used to enhance uptake.

"Targeted delivery" involves the use of targeting ligands which specifically enhance translocation of a nucleic acid to specific tissues or cells. Examples of cells which may be targeted include, but are not limited to, antigen-presenting cells, hepatocytes, myocytes, eptithelial cells, endothelial cells, and cancer cells.

A "target" is a specific organ, tissue, cell, or cellular region for which uptake of a vector and expression of a gene product is intended.

"Uptake" means the translocation of the vector from the extracellular to intracellular compartments. This can involve receptor mediated processes, fusion with cell membranes, endocytosis, potocytosis, pinocytosis or other translocation mechanisms. The vector may be taken up by itself or as part of a complex.

"Binding" is an intermediate step in uptake of some complexes involving a high-affinity interaction between a targeting ligand and a surface receptor on a target cell.

"Intracellular trafficking" is the translocation of the vector within the cell from the point of uptake to the nucleus where expression of a gene product takes place. Alternatively, cytoplasmic expression of a nucleic acid construct utilizing, for example, a T7 polymerase system may be accomplished. Various steps in intracellular trafficking include endosomal release and compartmentalization of the vector within various extranuclear compartments, and nuclear entry.

"Endosomal release" is the egress of the vector from the endosome after endocytosis. This is an essential and potentially rate limiting step in the trafficking of vectors to the nucleus. A lytic peptide may be used to assist in this process.

A "lytic peptide" is a peptide which functions alone or in conjunction with another compound to penetrate the membrane of a cellular compartment, particularly a lysosomal or endosomal compartment, to allow the escape of the contents of that compartment to another cellular compartment such as the cytosolic and/or nuclear compartment.

"Compartmentalization" is the partitioning of vectors in different compartments within a defined extracellular or intracellular space. Significant extracellular compartments may include, for example, the vascular space, hair follicles, interstitial fluid, synovial fluid, cerebral spinal fluid, thyroid follicular fluid. Significant intracellular compartments may include endosome, potosome, lysosome, secondary lysosome, cytoplasmic granule, mitochondria, and the nucleus.

"Nuclear entry" is the translocation of the vector across the nuclear membrane into the nucleus where the gene may be transcribed.

"Elimination" is the removal or clearance of materials (vectors, transcripts, gene products) from a specific compartment over time. This term may be used to reflect elimination from the body, the vascular compartment, extracellular compartments, or intracellular compartments. Elimination includes translocation (excretion) from a particular compartment or biotransformation (degradation).

The compounds which protect the nucleic acid and/or prolong the localized bioavailability of a nucleic acid may achieve one or more of the following effects, due to their physical, chemical or Theological properties: (1) Protect nucleic acid, for example plasmid DNA, from nucleases due to steric, viscosity, or other effects; (2) increase the area of contact between nucleic acid, such as plasmid DNA, through extracellular matrices and over cellular membranes, into which the nucleic acid is to be taken up; (3) concentrate nucleic acid, such as plasmid DNA, at cell surfaces due to water exclusion; (4) indirectly facilitate uptake of nucleic acid, such as plasmid DNA, by disrupting cellular membranes due to osmotic, hydrophobic or lytic effects; and (5) indirectly facilitate uptake of nucleic acids by allowing diffusion of protected nucleic acid chains through tissue at the administration site.

The following polymers, oils and surfactants may be suitable for use as compounds which prolong the localized bioavailability of a nucleic acid: polyvinylpyrrolidones; polyvinylalcohols; propylene glycols; polyethylene glycols; polyvinylacetates; poloxamers (Pluronics)(block copolymers of propylene oxide and ethylene oxide, relative amounts of the two subunits may vary in different poloxamers); poloxamines (Tetronics); ethylene vinyl acetates; celluloses, including salts of carboxymethylcelluloses, methylcelluloses, hydroxypropylcelluloses, hydroxypropylmethylcelluloses; salts of hyaluronates; salts of alginates; heteropolysaccharides (pectins); dextrans; chitosans; phosphatidylcholines (lecithins); miglyols; polylactic acid; polyhydroxybutyric acid. As indicated below, certain of these compounds may be used as protective, interactive, non-condensing compounds and others as sustained release compounds, while some may be used in either manner under the respectively appropriate conditions.

These substances may be prepared as solutions, suspensions, gels, emulsions or microemulsions of a water/oil (w/o), water/oil/water (w/o/w), oil/water (o/w) or oil/water/oil (o/w/o) type. Oil suspensions of lyophilized nucleic acid, such as plasmid DNA may be utilized. Carriers for these oil suspensions include, but are not limited to, sesame oil, cottonseed oil, soybean oil, lecithins, Tweens, Spans and Miglyols.

By "solutions" is meant water soluble polymers and/or surfactants in solution with nucleic acids.

By "suspensions" is meant water insoluble oils containing suspended nucleic acids.

By "gels" is meant high viscosity polymers containing nucleic acids.

By "emulsion" is meant a dispersed system containing at least two immiscible liquid phases. Emulsions usually have dispersed particles in the 0.1 to 100 micron range. They are typically opaque and thermodynamically unstable. Nucleic acids in the water phase can be dispersed in oil to make a w/o emulsion. This w/o emulsion can be dispersed in a separate aqueous phase to yield a w/o/w emulsion. Alternatively, a suitable oil could be dispersed in an aqueous phase to form an o/w emulsion. A "microemulsion" has properties intermediate to micelles and emulsions and is characterized in that they are homogenous, transparent and thermodynamically stable. They form spontaneously when oil, water, surfactant and cosurfactant are mixed together. Typically, the diameter of the dispersed phase is 0.01 to 0.1 microns, usually of the w/o and o/w type.

Some compounds which prolong the bioavailability of a nucleic acid may also interact or associate with the nucleic acid by intermolecular forces and/or valence bonds such as: Van der Waals forces, ion-dipole interactions, ion-induced dipole interactions, hydrogen bonds, or ionic bonds. These interactions may serve the following functions: (1) Stereoselectively protect nucleic acids from nucleases by shielding; (2) facilitate the cellular uptake of nucleic acid by "piggyback endocytosis". Piggyback endocytosis is the cellular uptake of a drug or other molecule complexed to a carrier that may be taken up by endocytosis. CV Uglea and C Dumitriu-Medvichi, Medical Applications of Synthetic Oligomers, In: *Polymeric Biomaterials*, Severian Dumitriu ed., Marcel Dekker, Inc., 1993, incorporated herein by reference.

To achieve the desired effects set forth it is desirable, but not necessary, that the compounds which prolong the bioavailability of a nucleic acid have amphiphilic properties; that is, have both hydrophilic and hydrophobic regions. The hydrophilic region of the compounds may associate with the largely ionic and hydrophilic regions of the nucleic acid, while the hydrophobic region of the compounds may act to retard diffusion of nucleic acid and to protect nucleic acid from nucleases.

Additionally, the hydrophobic region may specifically interact with cell membranes, possibly facilitating endocytosis of the compound and thereby also of nucleic acid associated with the compound. This process may increase the pericellular concentration of nucleic acid.

Agents which may have amphiphilic properties and are generally regarded as being pharmaceutically acceptable are the following: polyvinylpyrrolidones; polyvinylalcohols; polyvinylacetates; propylene glycol; polyethylene glycols; poloxamers (Pluronics); poloxamines (Tetronics); ethylene vinyl acetates; methylcelluloses, hydroxypropylcelluloses, hydroxypropylmethylcelluloses; heteropolysaccharides (pectins); chitosans; phosphatidylcholines (lecithins); miglyols; polylactic acid; polyhydroxybutyric acid; xanthan gum. Also, copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine (or pyrimidine) derivatives and N-vinylpyrrolidone. However, not all of the above compounds are protective, interactive, non-condensing compounds as described below.

In a first aspect, the invention provides compositions for the delivery of a nucleic acid to a cell. Such a composition includes a protective, interactive, non-condensing, amphiphilic compound (PINC) and a nucleic acid molecule. The PINC enhances the delivery of the nucleic acid molecule to mammalian cells in vivo, and preferably the nucleic acid molecule includes a coding sequence for a gene product to be expressed in the cell. In many cases, the relevant gene product is a polypeptide or protein.

In a related aspect, the invention also provides compositions for delivery of a nucleic acid molecule to a cell. As in the preceding aspect, the composition includes a PINC and a nucleic acid molecule. Also as in the preceding aspect, preferably the PINC is used under conditions so that the PINC does not form a gel, or so that no gel form is present at the time of administration at about 30–40° C. Thus, in these compositions, the PINC is present at a concentration of 30% (w/v) or less. In certain preferred embodiments, the PINC concentration is still less, for example, 20% or less, 10% or less, 5% or less, or 1% or less. Thus, these compositions differ in compound concentration and functional effect from uses of these or similar compounds in which the compounds are used at higher concentrations, for example in the ethylene glycol mediated transfection of plant protoplasts, or the formation of gels for drug or nucleic acid delivery. In general, the PINCs are not in gel form in the conditions in which they are used as PINCs, though certain of the compounds may form gels under some conditions.

In connection with the protective, interactive, non-condensing compounds for these compositions, the term "non-condensing" means that an associated nucleic acid is not condensed or collapsed by the interaction with the PINC at the concentrations used in the compositions. Thus, the PINCs differ in type and/or use concentration from such condensing polymers. Examples of commonly used condensing polymers include polylysine, and cascade polymers (spherical polycations).

Also in connection with such compounds and an associated nucleic acid molecule, the term "enhances the delivery" means that at least in conditions such that the amounts of PINC and nucleic acid is optimized, a greater biological effect is obtained than with the delivery of nucleic acid in saline. Thus, in cases where the expression of a gene product encoded by the nucleic acid is desired, the level of expression obtained with the PINC:nucleic acid composition is greater than the expression obtained with the same quantity of nucleic acid in saline for delivery by a method appropriate for the particular PINC/coding sequence combination.

In preferred embodiments of the above compositions, the gene product is a ribonucleic acid molecule, a polypeptide, or protein.

Also in preferred embodiments of the above compositions, the PINC is polyvinyl pyrrolidone (PVP), polyvinyl alcohol (PVA), a PVP-PVA co-polymer, N-methyl-2-pyrrolidone (NM2P), ethylene glycol, or propylene glycol. In compositions in which a Poloxamer (Pluronics) is used, the nucleic acid is preferably not a viral vector, i.e., the nucleic acid is a non-viral vector.

In other preferred embodiments, the PINC is bound with a targeting ligand. Such targeting ligands can be of a variety of different types, including but not limited to galactosyl, fucosal residues, mannosyl residues, carntitine derivatives, monoclonal antibodies, polyclonal antibodies, peptide ligands, and DNA-binding proteins. The targeting ligands may bind with receptors on cells such as antigen-presenting cells, hepatocytes, myocytes, epithelial cells, endothelial cells, and cancer cells.

In connection with the association of a targeting ligand and a PINC, the term "bound with" means that the parts have an interaction with each other such that the physical association is thermodynamically favored, representing at least a local minimum in the free energy function for that association. Such interaction may involve covalent binding, or non-covalent interactions such as ionic, hydrogen bonding, van der Waals interactions, hydrophobic interactions, and combinations of such interactions.

While the targeting ligand may be of various types, in one embodiment the ligand is an antibody. Both monoclonal antibodies and polyclonal antibodies may be utilized.

The nucleic acid may also be present in various forms. Preferably the nucleic acid is not associated with a compound(s) which alter the physical form, however, in other embodiments the nucleic acid is condensed (such as with a condensing polymer), formulated with cationic lipids, formulated with peptides, or formulated with cationic polymers.

As the compositions are useful for delivery of a nucleic acid molecule to cells in vivo, in a related aspect the invention provides a composition at an in vivo site of administration. In particular this includes at an in vivo site in a mammal.

In preferred embodiments the nucleic acid molecule includes a sequence encoding a gene product. Also in preferred embodiments, the site of administration is in an interstitial space or a tissue of an animal, particularly of a mammal.

The invention also provides methods for using the above compositions. Therefore, in further related aspects, methods of administering the compositions are provided in which the composition is introduced into a mammal, preferably into a tissue or an interstitial space.

Various methods of delivery may be utilized, such as are known in the art, but in preferred embodiments, the composition is introduced into the tissue or interstitial space by injection. The compositions may also be delivered to a variety of different tissues, but in preferred embodiments the tissue is muscle or tumor.

In another related aspect, the invention provides methods for treating a mammalian condition or disease by administering a therapeutically effective amount of a composition as described above. In preferred embodiments, the disease or condition is a cancer.

A "therapeutically effective amount" of a composition is an amount which is sufficient to cause at least temporary relief or improvement in a symptom or indication of a disease or condition. Thus, the amount is also sufficient to cause a pharmacological effect. The amount of the composition need not cause permanent improvement or improvement of all symptoms or indications.

In another aspect of the invention, the compound which prolongs the bioavailability of a nucleic acid is a sustained-release compound which may be administered to an organism or to cells in culture. The sustained-release compound containing a nucleic acid is administered to the tissue of an organism, for example, by injection. In one embodiment the tissue is preferably muscle tissue. In another embodiment the tissue is preferably a joint space. In another embodiment the tissue is preferably a tumor.

By "sustained-release compound" is meant a substance with a viscosity above that of an isotonic saline solution (150 mM NaCl) containing a nucleic acid; for example, DNA in saline at 1 mg/ml has a viscosity of 3.01 mPa·sec, DNA in saline at 2 mg/ml has a viscosity of 3.26 mPa·sec, DNA in saline at 3 mg/ml has a viscosity of 5.85 mPa·sec (Viscosity measurements were performed at 25° C. in a Brookfield DV-III Rheometer with a No. 40 Spindle at 75 rpm for 30 minutes).

Preferably the sustained-release compound has a viscosity in the range of about 0.1–20,000 mPa·sec above that of a formulation in which isotonic saline is the carrier for a nucleic acid. More preferably the range is about 0.1–5000 mPa·sec above that of a formulation in which isotonic saline is the carrier for a nucleic acid. Even more preferably the range is about 0.1–1000 mPa·sec above that of a formulation in which isotonic saline is the carrier for a nucleic acid.

By "sustained-release" is meant that nucleic acid is made available for uptake by surrounding tissue or cells in culture for a period of time longer than would be achieved by administration of the nucleic acid in a less viscous medium, for example, a saline solution.

In another embodiment, the compound which prolongs the bioavailability of a nucleic acid is a thermo-reversible gel.

By "thermo-reversible gel" is meant a gel which is substantially liquid at temperatures below about 30° C. but forms a gel at temperatures above about 30° C. Administration of the thermo-reversible gel by, for example, injection is thereby facilitated if the gel is cooled so that it is in a substantially liquid state when injected. However, upon contact with the tissue of an organism which is at a temperature of above about 30° C. the viscosity of the thermo-reversible gel increases, thereby increasing the localized bioavailability of a nucleic acid formulated with the thermo-reversible gel.

In another embodiment of the present invention, the molecules of the compound which prolongs the localized bioavailability of a nucleic acid tend to orient themselves in the direction of an induced flow and as an applied force causing the flow is increased and the resistance of the compound to flow is decreased, lowering an initial viscosity of the compound. When the applied force is removed, the compound substantially reverts to its initial viscosity. In a preferred embodiment the compound utilized is a salt of carboxymethylcellulose, such as sodium carboxymethylcellulose. Sodium carboxymethylcellulose has been used by the cosmetics, food, and pharmaceutical industries as a stabilizer, thickener, gelling agent, suspending agent, and a lubricant. Sodium carboxymethyl cellulose is an approved pharmaceutical excipient.

In another embodiment, the compound which prolongs the bioavailability of a nucleic acid is polyvinylpyrrolidone (PVP). PVP is a polyamide that forms complexes with a wide variety of substances and is chemically and physiologically inert. Specific examples of suitable PVP's are Plasdone-C®15, MW 10,000 and Plasdone-C®30, MW 50,000.

In another embodiment the compound which prolongs the bioavailability of a nucleic acid is an oily suspension. By "oily suspension" is meant a coarse dispersion containing finely divided insoluble material suspended in a liquid medium. These formulations include: nucleic acids, polymers, peptides or sugars and are dispersed with the aid of a dispersing agent, such as a surfactant in a suitable vehicle such as an oil. For example, DNA/PVP powder blend in Miglyol with 0.1% Tween-80, DNA/PVP powder blend in sesame oil with 0.1% Tween-80, DNA/lactose powder blend in Miglyol with 0.1% Tween-80, DNA complex powder blends in Miglyol with 0.1% Tween-80, where the DNA complex could comprise condensed DNA complexes such as DNA:polymer or DNA:peptide.

In another embodiment the compound which prolongs the bioavailability of a nucleic acid is a water-in-oil microemulsion. Examples would include: lecithin:sesame oil:butanol (surfactant/oil/cosurfactant) as the oil phase with DNA in saline as the water phase; lecithin:sesame oil:butanol (surfactant/oil/cosurfactant) as the oil phase with DNA complex saline as the water phase.

In another embodiment the compound which prolongs the bioavailability of a nucleic acid is a hydrogel. Nucleic acids may be loaded into hydrogels by placing swellable hydrogel systems in nucleic acid solutions. Swellable hydrogels include but are not limited to hydroxyethylmethacrylate (HEMA), polyethyleneglycolmethacrylate (PEGMA), cellulose ether hydrogels, comprising cross-linked hydroxypropyl cellulose, methyl cellulose, and hydroxypropylmethyl cellulose; calcium-crosslinked alginate; crosslinked polyvinyl alcohols and Poloxamers (Pluronics).

In another embodiment the compound which prolongs the bioavailability of a nucleic acid is a cationic polymer, such as Eudragit, Chitosan and Poloxamines (Tetronics).

In another embodiment the compound which prolongs the bioavailability of a nucleic acid is a surfactant which forms micelles, such as Tween 80.

In another embodiment the uptake of nucleic acids in vitro, for example, cells in tissue culture is enhanced by the use of the compounds disclosed herein.

Other and further objects, features, and advantages will be apparent from the following description of the presently preferred embodiments in the invention.

BRIEF DESCRIPTION OF THE DRAWINGS

FIG. 1 illustrates a plot of the fraction of PVP:DNA at different ratios remaining within a dialysis sac over time.

FIG. 2 illustrates the transfection efficiency into $C_2C_{12}$ myoblasts of a plasmid DNA complex administered with various polymers and controls comprising a polymer alone, and a pDNA complex alone.

FIG. 3 illustrates the transfection efficiency into $C_2C_{12}$ myoblasts when transfected with plasmid DNA in 10%, 20%, and 30% PEG (8 kDa) with and without the presence of an endosomal release peptide (lytic peptide).

FIG. 11 is a bar graph showing the relative reporter gene (CAT) expression levels in solid tumors for 5 PINC formulations, DOTMA/chol, and saline.

Figure 4:
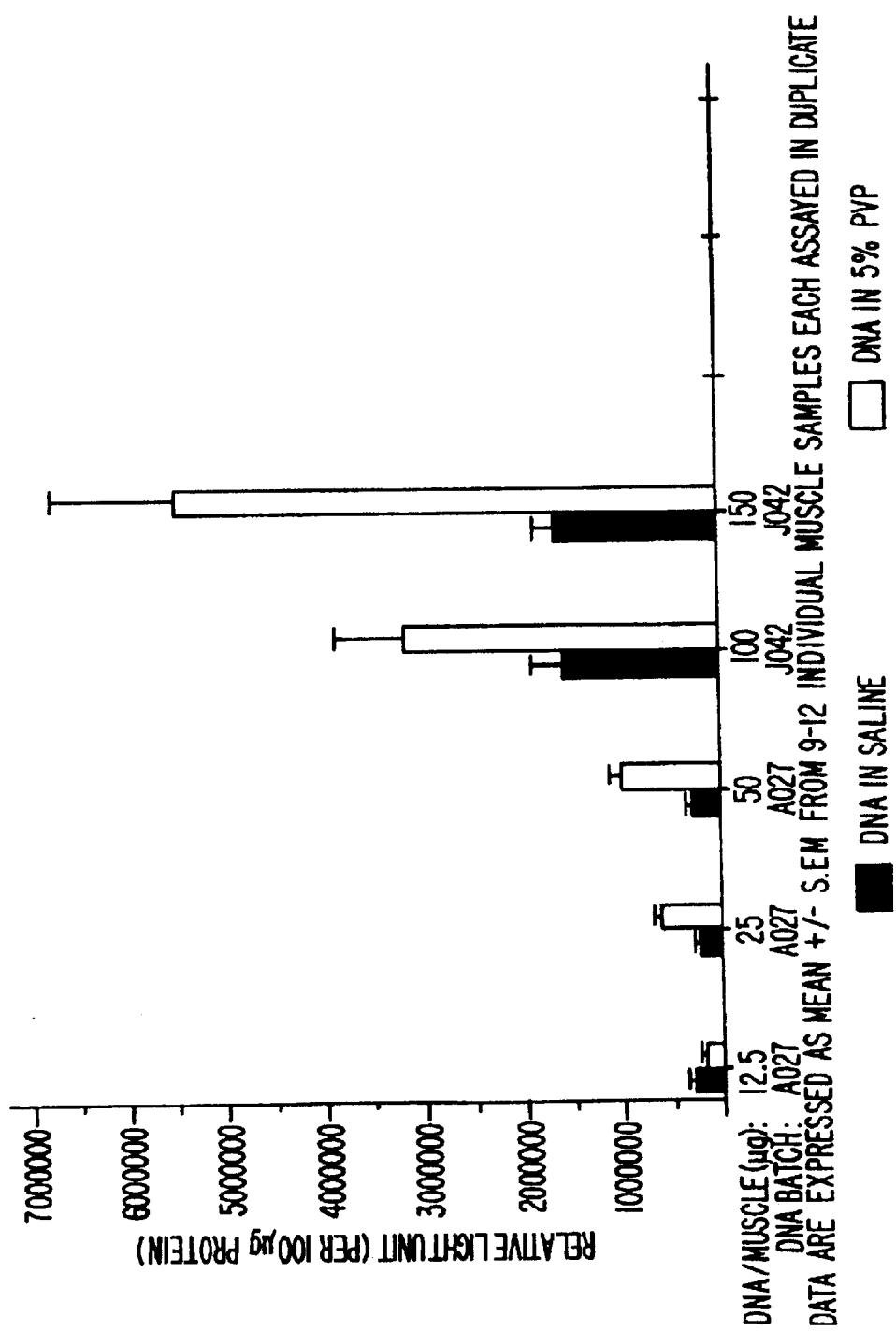
FIG. 4 illustrates the magnitude of β-galactosidase marker gene expression when a plasmid containing the marker gene is administered in saline or a PVP formulation.

The drawings are not necessarily to scale. Certain features of the invention may be exaggerated in scale or shown in schematic form in the interest of clarity and conciseness.

DETAILED DESCRIPTION OF THE PREFERRED EMBODIMENTS

The delivery and expression of sequences encoded on a vector in eukaryotic cells, particularly in vivo in a mammal, depends on a variety of factors including transfection efficiency and lifetime of the coding sequence within the transfected cell. Thus, a number of methods are reported for accomplishing such delivery. In the particular context of delivery to muscle tissue, the use of DNA formulated in saline is reported. Such reports provide useful contrast for understanding the present invention, and also discuss particular aspects of administration relating to direct injection.

I. Use of DNA:Saline Formulations

Of at least 20 variables which have been studied for their effects on the delivery and expression of DNA:saline formulations, only a few have been found to have large effects. A summary of the studied variables is presented in Table 1 below.

Table 1: Injection Variables Investigated for Plasmid Delivery to Muscle

| | |
|---|---|
| High Significance on Expression (>5-fold effect) | |
| Formulation | Mumper 1996 [46], Mumper 1997 [47], Manthorpe 1993 [63], Davis 1993 [65], Wolff 1991 [66], Wolff 1992 [67] |
| Animal species | Jiao 1992 [68] |
| Dose | Levy 1996 [16], Wolff 1990 [1], Mumper 1996 [46], Manthorpe 1993 [63], Davis 1993 [65], Jiao 1992 [68], |
| Injection angle or needle manipulation | Levy 1996 [16] |
| Pretreatment with myotoxic agents | Vitadello 1994 [69], Danko 1994 [70], Davis 1993 [71], Wells 1993 [72] |
| State of muscle (i.e., stimulated, contracted, massaged) | Davis 1993 [65], Wolff 1991 [66], Dowty 1994 [73] |
| Plasmid topology | Manthorpe 1993 [63], Wolff 1991 [66], Wolff 1992 [67] |
| Moderate Significance on Expression (>2-fold effect) | |
| Injection volume | Davis 1993 [65], Manthorpe 1993 [63], Wolff 1991 [66] |
| Plasmid implantation | Wolff 1991 [66], Jiao 1992 [68] |
| Animal age | Wells 1992 [74], Manthorpe 1993 [63] |
| Animal sex | Wells 1992 [74] |
| Low or No Significance on Expression (<2-fold effect) | |
| Multi-Injection | Jiao 1992 [68], Manthorpe 1993 [63] |
| Muscle type | Jiao 1992 [68] |
| Needle gauge | Manthorpe 1993 [63] |

-continued

| | |
|---|---|
| Injection speed | Manthorpe 1993 [63], Wolff 1991 [66] |
| Denervation | Wolff 1991 [66] |
| Number of injection sites | Manthorpe 1993 [63], Jiao 1992 [68] |
| Temperature of injection fluid | Manthorpe 1993 [63] |

References

1 Wolff, J. A., Malone, R. W., Williams, P., Chong, W., Acsadi, G., and Jani, A. (1990). Direct gene transfer into mouse muscle in vivo. Science. 247, 1465–68.

5 Acsadi, G., Dickson, G., Love, D. R., Jani, A., Walsh, F. S., and Wolff, J. A. (1991). Human dystrophin expression in mdx mice after intramuscular injection of DNA constructs. Nature. 352, 815–18.

6 Karpati, G., and Acsadi, G. (1993). The potential for gene therapy in Duchenne Muscular Dystrophy and other genetic muscle diseases. Muscle Nerve. 16, 1141–53.

7 Miller, J. B., and Boyce, F. M. (1995). Gene therapy by and for muscle cells. Trends Genet. 11, 163–65.

8 Coleman, M. E., Criswell, D., Booth, F. W., and Alila, H. A. (1997). Non-viral IGF-1 gene therapy reduces atrophy and loss of muscle strength in tibialis anterior muscles of hindlimb suspended mice. Submitted to American J. Phys.

9 Alila, H., Coleman, M., French, M., Nitta, H., Liu, Q., Wang, J., Nordstrom, J., and Rolland, A. (1997). Expression of biologically active human insulin-like growth factor-I following intramuscular injection of a formulated DNA plasmid in rats. Submitted to Hum. Gene Therapy.

10 Rabinovsky, E., Kataash, M., Nitta, H., Alila, H., Liu, Q., Meyer, T., Schwartz, R., and Coleman, M. (1997). Non-viral gene therapy enhances recovery following sciatic nerve crush. Submitted to Nature Medicine.

11 Anwer, K. Shi, M., French, M. F., Muller, S. R., Chen, W., Liu, Q., Thompson, B. L., Wang, J., Mumper, R. J., Rolland, A. P., and Alila, H. (1997). Systemic effect of human growth hormone after intramuscular injection of a single dose of a muscle-specific gene medicine. Submitted to Nature Medicine.

12 Kuwahara-Rundell, A. Y., Margalith, M., Rhodes, G., Yankauckas, M., and Dwarki, V. J. (1994). Expression of dog Factor-IX protein after intramuscular DNA injections in mice. J. Cell. Biochem. Suppl. 18A, 233.

13 Miller, G., Steinbrecher, R. A., Murdock, P., Pasi, K. J., Tuddenham, E. G. D., Lee, C. A., and Goldspink, G. (1994). Expression of Factor-VII in vitro and in vivo following direct gene transfer into muscle: a model for hemophilia. Gene Ther.; 1, Suppl. 2, S16.

14 Tripathy, S. K., Svensson, E. C., Black, H. B., Goldwasser, E., et al. Long-term expression of erythropoietin in the systemic circulation of mice after intramuscular injection of a plasmid DNA vector. Proc. Natl. Acad. Sci. 93, 10876–10880.

15 Dahler, A., Wade, R. P., Muscat G. E. O., and Waters, M. J. (1994). Expression vectors encoding human growth hormone (hGH) controlled by human muscle-specific promoters: prospects for regulated production of hGH delivered by myoblast transfer or intravenous injection. Gene 145, 305–310.

16 Levy, M. Y., Barron, L. G., Meyer, K. B., and Szoka, F. C. (1996). Characterization of plasmid DNA transfer into mouse skeletal muscle: evaluation of uptake mechanism, expression and secretion of gene products into blood. Gene Therapy. 3, 201–211.

17 Raz, E., Watanabe, A., Baird, S. M., Eisenberg, R. A., Parr, T. B., Lotz, M., Kipps, T. J., and Carson, D. A. (1993). Systemic immunological effects of cytokine genes injected into skeletal muscle. Proc. Natl. Acad. Sci. 90, 4523–7.

18 Fazio, V. M., Fazio, S., Rinaldi, M., Catani, M. V., Zotti, S., and Ciafre, S. A. (1994). Accumulation of human apolipoprotein-E in rat plasma after in vivo intramuscular injection of naked DNA. Biochem. Biophys. Res. Commun. 200, 298–305.

19 Ma, J., Yang, Z., Chao, J., and Chao, L. (1995). Intramuscular delivery of rat kallikrein-binding protein gene reverses hypotension in transgenic mice expressing human tissue kallikrein. J. Biol. Chem. 270, 451–455.

20 Xiong, W., Chao, J., and Chao, L. (1995). Muscle delivery of human kallikrein gene reduces blood pressure in hypertensive rats. Hypertension. 25, 715–19.

21 Manickan, E., Rouse, R. J., Yu, Z., Wire, W. S., and Rouse, B. T. (1995). Genetic immunization against herpes simplex virus. Protection is mediated by CD4+ T lymphocytes. J. Immunol. 155, 259–265.

22 Ghiasi, H., Cai, S., Slanina, S., Nesbum, A. B., and Wechsler, S. L. (1995). Vaccination of mice with herpes simplex virus type 1 glycoprotein D DNA produces low levels of protection against lethal HSV-1 challenge. Antiviral Res. 28, 147–57.

23 McClements, W. L., Armstrong, M. E., Keys, R. D., and Liu, M. A. (1996). Immunization with DNA vaccines encoding glycoprotein D or glycoprotein B, alone or in combination, induces protective immunity in animal models of herpes simplex virus-2 disease. Proc. Natl. Acad. Sci. 93, 11414–11420.

24 Kriesel J. D, Spruance, S. L., Daynes, R. A., and Araneo, B. A. (1996). Nucleic acid vaccine encoding gD2 protects mice from herpes simplex virus type 2 disease. J. Inf. Dis. 173, 536–541.

25 Davis, H. L., McCluskie, M. J., Gerin, J. L., and Purcell, R. H. (1996). DNA vaccine for hepatitis B: evidence for immunogenicity in chimpanzees and comparison with other vaccines. Proc. Natl. Acad. Sci. 93, 7213–7218.

26 Davis, H. L., Michel, M. L., and Whalen, R. G. (1993) DNA-based immunization for hepatitis B induces continuous secretion of antigen and high levels of circulating antibody. Human Molec. Genet. 2, 1847–1851.

27 Davis, H. L., Michel, M. L., Mancini, M. Schleef, M. and Whalen, R. G. (1994). Direct gene transfer in skeletal muscle: plasmid DNA-based immunization against the hepatitis B virus surface antigen. Vaccine. 12, 1503–09.

28 Donnelly, J. J., Friedman, A., Martinez, D., Montgomery, D. L., et al. (1995). Preclinical efficacy of a prototype DNA vaccine: enhanced protection against antigenic drift in influenza virus. Nat. Med. 1, 521–2.

29 Ulmer, J. B., Donnelly, J. J., Parker, S. E., Rhodes, G. H., Felgner, P. L., et al. (1993). Heterologous protection against influenza by injection of DNA encoding a viral protein. Science. 259, 1745–1749.

30 Ulmer, J. B., Deck, R. R., DeWitt, C. M., Friedman, A., Donnelly, J. J., and Liu, M. A. (1994). Protective immunity by intramuscular injection of low doses of influenza DNA vaccines. Vaccine. 12, 1541–44.

31 Lowrie, D. B., Tascon, R. E., Colston, M. J., and Silva, C. L. (1994). Towards a DNA vaccine against tuberculosis. Vaccine. 12, 1537–40.

32 Tascon, R. E., Colston, M. J., Ragno, S., Stavropoulos, E., Gregory, D., and Lowrie, D. B. (1996). Vaccination against tuberculosis by DNA injection. Nat. Med. 2, 888–892.

-continued

33 Shiver, J. W., Perry, H. C., Davies, M. E., Freed, D. C., and Liu, M. A. (1995). Cytotoxic T lymphocyte and helper T cell responses following HIV polynucleotide vaccination. Ann. N.Y. Acad. Sci. 772, 198–208.
34 Coney, L., Wang, B., Ugen, K. E., Boyer, J. et al. (1994). Facilitated DNA inoculation induces anti-HIV-1 immunity in vivo. Vaccine. 12, 1545–50.
35 Wang, B., Ugen, K. E., Srikantan, V., Agadjanyan, M. G., et al. (1993). Gene inoculation generates immune responses against human immunodeficiency virus type 1. Proc. Natl. Acad. Sci. 90, 4156–4160.
36 Russell, S. J., Winter, G, Stevenson, F. K., Hamblin, T. J., and Hawkins, R. E. (1994). Plasmid vaccination to elicit anti-idiotypic immune responses against surface immunoglobulin-positive B-cell malignancies. Br. J. Haematol. 86, Suppl. 1, 74.
37 Hoffman, S. L., Doolan, D. L., Sedegah, M., Gramzinski, R., et al. (1995). Nucleic acid malaria vaccines. Current status and potential. Ann. N.Y. Acad. Sci. 772, 88–94.
38 Sedegah, M, Hedstrom, R., Hobart, P., and Hoffman, S. L. (1994). Protection against malaria by immunization with circumsporozoite protein plasmid DNA. Proc. Natl. Acad. Sci. 91, 9866–9870.
39 Major, M. E., Vitvitski, L., Mink, M. A., Schleef, M., et al. (1995). DNA-based immunization with chimeric vectors for the induction of immune responses against the hepatitis C virus nucleocapsid. J. Virol. 69, 5798–805.
40 Lagging, L. M., Meyer, K., Hoft, D., Houghton, M., Belshe, R. B., and Ray, R. (1995). Immune response to plasmid DNA encoding the hepatitis C virus core protein. J. Virol. 69, 5859–63.
41 Phillpotts, R. J., Venugopal, K., and Brooks, T. (1996). Immunization with DNA polynucleotides protects mice against lethal challenge with St. Louis encephalitis virus. Arch. Virol. 141, 743–49.
42 Pande, H., Campo, K., Tanamachi, B., Forman, S. J., and Zaia, J. A. (1995). Direct DNA immunization of mice with plasmid DNA encoding the tegument protein pp65(ppUL83) of human cytomegalovirus induces high levels of circulating antibody to the encoded protein. Scand. J. Infect. Dis. Suppl. 99, 17–120.
43 Lopez-Macias, C., Lopez-Hernandez, M. A., Gonzalez, C. R., Isibasi, A., and Ortiz-Navarrete, V. (1995). Induction of antibodies against Salmonella typhi OmpC porin by naked DNA immunization. Ann. N.Y. Acad. Sci. 772, 285–8.
44 Lai, W. C., Bennet, M., Johnston, S. A., Barry, M. A., and Pakes, S. P. (1995). Protection against Mycoplasma pulmonis infection by genetic vaccination. DNA Cell Biol. 14, 643–51.
45 Xiang, Z. Q., Spitalnik, S. L., Cheng, J., Erikson, J., Wojczyk, B., and Ertl, H. C. (1995). Immune response to nucleic acid vaccines to rabies virus. Virology 209, 569–79.
46 Mumper, R. J., Duguid, J. G., Anwer, K., Barron, M. K., Nitta, H., and Rolland, A. P. (1996). Polyvinyl derivatives for controlled gene delivery to muscle. Pharm. Res. 13, 701–709.
47 Mumper, R. J., Wang, J., Nitta, H., Anwer, K., Tagliaferri, F., and Rolland, A. P. (1997). Protective Interactive Non-Condensing (PINC) Polymers for Enhanced Plasmid Distribution and Expression in Rat Skeletal Muscle. Submitted to Gene Therapy.
63 Manthorpe, M., Cornefert-Jensen, F., Hartikka, J., Felgner, J., Rundell, A., Margalith, M., and Dwarki, V. (1993). Gene therapy by intramuscular injection of plasmid DNA: studies on firely luciferase gene expression in mice. Hum. Gene Ther. 4, 419–31.
65 Davis, H. L., Whalen, R. G., and Demeneix, B. A. (1993). Direct gene transfer into skeletal muscle in vivo: factors affecting efficiency of transfer and stability of expression. Hum. Gene Ther. 4, 151–9.
66 Wolff, J. A., Williams, P., Acsadi, G., Jiao, S., Jani, A., and Chong, W. (1991). Conditions affecting direct gene transfer into rodent muscle in vivo. BioTechniques. 11, 474–85.
67 Wolff, J. A., Dowty, M. E., Jiao, S., Repetto, G. et al. (1992). Expression of naked plasmids by cultured myotubes and entry of plasmids into T tubules and caveolae of mammalian skeletal muscle. J. Cell. Sci. 103, 1249–1259.
68 Jiao, S., Williams, P., Berg, R. K., Hodgeman, B. A., Liu, L., Repetto, G., and Wolff, J. A. (1992). Direct gene transfer into nonhuman primate myofibers in vivo. Hum. Gene Ther. 3, 21–33.
69 Vitadello, M., Schiaffino, M. V., Picard, A., Scarpa, M., and Schiaffino, S. (1994). Gene transfer in regenerating muscle. Hum. Gene Ther. 5, 11–18.
70 Danko, I., Fritz, J. D., Jiao, S., Hogan, K., Latendresse, J. S., and Wolff, J. A. (1994). Pharmacological enhancement of in vivo foreign gene expression in muscle. Gene Ther. 1, 114–121.
71 Davis, H. L., Demeneix, B. A., Quantin, B., Coulombe, J. and Whalen, R. G. (1993). Plasmid DNA is superior to viral vectors for direct gene transfer into adult mouse skeletal muscle. Hum. Gene Ther. 4, 733–40.
72 Wells, D. J. (1993). Improved gene transfer by direct plasmid injection associated with regeneration in mouse skeletal muscle. FEBS. Lett. 332, 179–82.
73 Dowty, M. E., and Wolff, J. A. (1994). Possible mechanisms of DNA uptake in skeletal muscle. In: J. A. Wolff (Ed.), Gene Therapeutics: Methods and Applications of Direct Gene Transfer. Birkhauser, Boston, pp. 82–98.
74 Wells, D. J., and Goldspink, G. (1992). Age and sex influence expression of plasmid DNA directly injected into mouse skeletal muscle. FEBS. Lett. 306, 203–5.

The variables found to have the highest significance (>5-fold effect over controls) on the levels of gene expression in the muscle are: i) the formulation (composition, plasmid topology), ii) the technique and protocol for injection (angle of injection, state of muscle), iii) the species being injected, and iv) the pretreatment of the muscle with myotoxic agents.

In connection with pretreatment and DNA:saline formulations, several papers describe the pretreatment of muscles with hypertonic sucrose prior to injection of plasmid formulated in saline [Wolff et al., 1990, Science 247:1465–68; Davis et al., 1993, Hum. Gene Ther. 4:151–9; Wolff et al., 1991, BioTechniques 11:474–85]. The preinjection of sucrose improves the intramuscular distribution of plasmid and results in reduced variability of gene expression. Further, staining for β-gal was more disperse in muscles that had been preinjected with sucrose. Muscles not preinjected with sucrose had staining that was highly variable. However, these solutions result in large areas of muscle damage.

In contrast to the many papers describing the use of sucrose preinjection, there have been very few papers describing formulations for plasmid other than saline [Mumper, R. J., et al., 1996, Pharm. Res. 13:701–709; Mumper, R. J., et al., 1997, Submitted to Gene Therapy; Manthorpe, M., et al., 1993, Hum. Gene Ther. 4:419–31; Wolff, J. A., et al., 1991, BioTechniques 11:474–85; Wolff, J. A., et al., 1992, J. Cell. Sci. 103:1249–1259]. Manthorpe et al. have investigated the co-injection of pharmacologically active drugs and plasmid [Manthorpe, M., et al., 1993, Hum. Gene Ther. 4:419–31]. Manthorpe et al. showed that mixing plasmid with a metabolic stimulant (ATP), muscle depolarizing agents (acetylcholine, succinylcholine, potassium chloride), and cationic peptides had no effect on gene expression in muscle over the control. However, the injection of plasmid in water (hypotonic vehicle) resulted in 95% lower gene expression in the muscle. Wolff et al. investigated the effect of formulating plasmid in various solutions and buffers on gene expression in muscle. [Wolff, J. A., et al., 1991, BioTechniques 11:474–85]. The results showed that no vehicle resulted in reproducible and/or enhanced levels of gene expression in muscle over plasmid formulated in saline.

Wolff et al. also showed that plasmid condensed with cationic lipid resulted in 100-fold less gene expression in muscle cells than with plasmid formulated in saline. These condensed plasmid complexes were found to not cross the external lamina and access the muscle cells. [Wolff, J. A., et al., 1992, J. Cell. Sci. 103:1249–1259].

Plasmid topology, or plasmid form, has also been shown to have an effect on the resulting gene expression in muscle cells [Manthorpe, M., et al., 1993, Hum. Gene Ther. 4:419–31; Wolff, J. A., et al., 1991, BioTechniques 11:474–85; Wolff, J. A., et al., 1992, J. Cell. Sci. 103:1249–1259]. In general, the injection of linear plasmid formulated in saline has been correlated with a decrease in gene expression in muscle. Although circular plasmid and linear plasmid have similar intramuscular distribution immediately following injection, the linear plasmid, except for a small amount near the injection site, was completely absent from muscle 1 hr after injection [Wolff, J. A., et al., 1992, J. Cell. Sci. 103:1249–1259]. Wolff et al. demonstrated that the injection of linear plasmid resulted in approximately 100-fold less activity as compared to open-circular and covalently closed-circular plasmid. It has been proposed by Wolff et al. that linear plasmid has an increased degradation rate in vivo. We have also observed that plasmids with different topologies formulated in saline resulted in differences in gene expression in muscle whereby mostly supercoiled plasmid resulted in the highest levels of gene expression.

Another injection variable that has been shown to effect significantly the levels of gene expression in muscle are both the state of the muscle being injected and the injection technique. Examples of the variables include muscle stimulation, muscle contraction, muscle massage, injection angle, and needle manipulation. Stimulating mouse muscle with 50-Hz, 12-V stimulus for 20 second periods alternating with 20 second rests over a 20 minute period prior to injecting plasmid resulted in a 7-fold decrease in luciferase expression. Wolff, J. A., et al., 1991, BioTechniques 11:474–85]. Muscle stimulation after injection of plasmid had no significant effect. Sustained muscle contraction prior to injection also decreased plasmid uptake. Dowty, M. E., and Wolff, J. A., 1994, In: J. A. Wolff (Ed.), Gene Therapeutics: Methods and Applications of Direct Gene Transfer, Birkhauser, Boston, pp. 82–98]. Likewise, massaging mouse muscle for 10–15 minutes after the injection of plasmid reduced the level of gene expression over 10-fold. Davis, H. L., et al., 1993, Hum. Gene Ther. 4:151–9]. It was postulated that massaging the muscle forced plasmid out of the muscle either directly or via lymphatic drainage. Levy et al. have reported that longitudinal injection of plasmid formulated in saline (needle is inserted parallel to the muscle fibers) results in up to a 200-fold increase in luciferase expression in mouse muscle as compared to when the plasmid is injected through a needle that is positioned perpendicular to the muscle fibers [Levy, M. Y., et al., 1996, Gene Therapy3:201–211]. This injection technique was said to improve the plasmid distribution throughout the muscle which subsequently increased the uptake of plasmid and gene expression.

We have also shown that longitudinal injection results in a similar enhancement of gene expression in muscle and have enhanced even further the levels of gene expression in muscle by employing a needle 'retraction/injection' method. The 'retraction/injection' consists of the insertion of the needle parallel to the muscle fibers with subsequent injection of the solution as the needle is being retracted. In a test, β-gal expression was determined 7 days after CMV-β-gal (150 μg/50 μL) plasmid, complexed with PVP (50 kDa) (1:17 w/w) and formulated in 150 mM NaCl, was injected into rat tibialis muscle using two different longitudinal injection methods. The results show that, using the 'retraction/injection' method, the levels of β-gal expression in rat tibialis muscle were 7-fold greater than when the formulation was injected using the normal longitudinal injection method. It is likely that the 'retraction/injection' method results in even further distribution of plasmid in muscle over the longitudinal method. However, due to the added technical difficulty of the 'retraction/injection' method, the method has not been our usual injection technique. For most studies involving muscle injection, we have utilized the longitudinal injection method [Mumper, R. J., et al., 1996, Pharm. Res. 13:701–709; Mumper, R. J., et al., 1997. Submitted to Gene Therapy].

Jiao et al. have demonstrated that there are marked differences in the level of gene expression after the administration of 100–500 μg RSV-luciferase plasmid to mouse, rat, cat, and rhesus monkey muscles [Jiao, S., et al., 1992, Hum. Gene Ther. 3:21–33]. The levels of luciferase expression 7 to 14 days post-injection were comparable in mouse and rat; three-fold lower in cat; and approximately 30-fold lower in monkey muscle. It was proposed that the lower level of gene expression found in monkey muscle was due to the considerable amount of connective tissue in monkey muscle. Using fluorescent WGA lectin, Jiao et al. showed that the perimysium in monkey muscle was approximately 2-fold thicker than the perimysium of rodents, whereas the endomysium thickness appeared to be similar between the species. Also, Wolff et al. found that after plasmid was injected into mouse muscle, plasmid was present throughout the entire width and length of the muscle [Wolff, J. A., et al., 1992, J. Cell. Sci. 103:1249–1259]. Approximately 80% of the muscle myofibers were in contact with the plasmid. In contrast, after administration of plasmid to monkey muscle, a greater amount of plasmid was found in the perimysium space and a decreased amount of plasmid was found in contact with myofibers in the endomysial space. Further, both the mouse and rat muscles were found to have a 50% increase in the number of nuclei per area of muscle as compared to monkey muscle. The decreased density of connective tissue and increased density of nuclei in rodent muscle may explain the increased levels of gene expression found in rodent muscle.

The uptake and gene expression of plasmid formulated in saline appears to be a saturable process that is largely dependent on the species and the formulation used for injection [Wolff, J. A., et al., 1990, Science 247:1465–68; Levy, M. Y., et al., 1996, Gene Therapy 3:201–211; Mumper, R. J., et al., 1996, Pharm. Res. 13:701–709; Jiao, S., et al., 1992, Hum. Gene Ther. 3:21–33; Manthorpe, M., et al., 1993, Hum. Gene Ther. 4:419–31; Davis, H. L., et al., 1993, Hum. Gene Ther. 4:151–9. For example, the plateau of gene expression in mice was between 25–100 μg plasmid injected [Wolff, J. A., et al., 1990, Science 247:1465–68;

Levy, M. Y., et al., 1996, *Gene Therapy* 3:201–211; Manthorpe, M., et al., 1993, *Hum. Gene Ther.* 4:419–31; Davis, H. L., et al., 1993, *Hum. Gene Ther.* 4:151–9]. In rat, the plateau of gene expression was 50–150 µg plasmid injected [Mumper, R. J., et al., 1996, *Pharm. Res.* 13:701–709]. In contrast, in monkey the gene expression was linear through 500 µg plasmid injected [Jiao, S., et al., 1992, *Hum. Gene Ther.* 3:21–33]. It is likely that a subsaturable amount of plasmid was injected into monkey muscle in this study so that a plateau in gene expression was not observed. Preinjection of hypertonic sucrose (either 20% or 25%) resulted in levels of gene expression in mouse muscle that continued to be linear at greater concentrations [Wolff, J. A., et al., 1990, *Science* 247:1465–68; Davis, H. L., et al., 1993, *Hum. Gene Ther.*4:151–9]. We have also found dose responses in muscle using PINC systems to be linear at higher concentrations of CMV-β-gal plasmid injected [Mumper, R. J., et al., 1996, *Pharm. Res.* 13:701–709].

DNA has been found to be expressed in skeletal muscle of various species for greater than 4–24 months [Hagstrom, J. E., et al., 1996, *Biochem. Mol. Med.* 58:113–121; Wolff, J. A., et al., 1996, *Hum. Mol. Genet.* 1:363–9; Manthorpe, M., et al., 1993, *Hum. Gene Ther.* 4:419–31; Jiao, S., et al., 1992, *Hum. Gene Ther.* 3:21–33]. The long duration of gene expression has been attributed to the persistence of the plasmid in the nuclei of myofibers. Gene expression was found to be unstable when mRNA was injected into muscle suggesting that persistence of gene expression was not due to persistence of transcript or protein [Hagstrom, J. E., et al., 1996, *Biochem. Mol. Med.* 58:113–121]. Peak levels of gene expression in muscle are usually found between 7–14 days [Levy, M. Y., et al., 1996, *Gene Therapy* 3:201–211; Mumper, R. J., et al., 1996, *Pharm. Res.* 13:701–709; Manthorpe, M., et al., 1993, *Hum. Gene Ther.* 4:419–31; Jiao, S., et al., 1992, *Hum. Gene Ther.* 3:21–33], but have been found in certain studies to be as long as 30–60 days post-injection [Hagstrom, J. E., et al., 1996, *Biochem. Mol. Med.* 58:113–121; Wolff, J. A., et al., 1992, *Hum. Mol. Genet.* 1, 363–9; Jiao, S., et al., 1992, *Hum. Gene Ther.* 3:21–33]. Another finding is that plasmid persists in the nucleus and appears to remain unintegrated, or extrachromosomal. Wolff et al. demonstrated that plasmid does not replicate in muscle cells since the methylation pattern of the plasmid remained in its bacterial form [Wolff, J. A., et al., 1992, *Hum. Mol. Genet.* 1, 363–9]. Also, no chromosomal integration of plasmid was found after electroporating the injected muscle into bacteria after restriction enzyme digestion and ligation. Lack of plasmid integration into chromosomes with plasmid-based gene therapy after intramuscular injection provides better control of gene expression over viral-based approaches and represent a safer method. plasmid persists in the nucleus and appears to remain unintegrated, or extrachromosal. Wolff et al. demonstrated that plasmid does not replicate in muscle cells since the methylation pattern of the plasmid remained in its bacterial form [Wolff, J. A., et al., 1992, *Hum. Mol. Genet.* 1, 363–9]. Also, no chromosomal integration of plasmid was found after electroporating the injected muscle into bacteria after restriction enzyme digestion and ligation. Lack of plasmid integration into chromosomes with plasmid-based gene therapy after intramuscular injection provides better control of gene expression over viral-based approaches and represent a safer method.

Wolff et al. reported that, up to 1 hr after intramuscular injection of plasmid formulated in saline into mouse quadricep muscles, plasmid was present throughout the entire length and width of the muscle [Wolff, J. A., et al., 1992, *J. Cell. Sci.* 103:1249–1259]. Further, the majority of muscle fibers (i.e., ~80% of the cells) were in contact with the plasmid, specifically the T tubules and caveolae. In contrast, the distribution of plasmid after administration to monkey quadriceps resulted in a larger percentage of the plasmid in the perimysium space and a lower percentage of the myofibers in contact with plasmid, as stated previously. The presence of plasmid throughout the mouse muscle suggests that plasmid is dispersed in muscle due to hydrostatic pressures. However, an implanted plasmid pellet also resulted in a similar distribution of plasmid throughout the entire muscle at 1 hr demonstrating that the dispersion of plasmid was not due to hydrostatic pressures. Three hours after injection of plasmid into mouse muscle much less plasmid was observed in the muscle as compared to 1 hr suggesting rapid removal of plasmid from 1–3 hours post-injection. The plasmid remaining in the muscle after 3 hours was largely in the caveolae and T tubules. Manthorpe et al. have also confirmed rapid removal of plasmid from muscle after the injection of plasmid formulated in saline. Their studies showed that greater than 95% of the plasmid appeared degraded by 90 minutes post-injection as determined by Southern blotting [Manthorpe, M., et al., 1993, *Hum. Gene Ther.* 4:419–31]. Levy et al. have demonstrated that 125-Iodine labeled plasmid was rapidly removed from mouse muscle after injection [Levy, M. Y., et al., 1996, *Gene Therapy* 3:201–211]. Only 40% of the administered dose remained in the muscle at 60 minutes post-injection and by 9 hours after injection, greater than 98% of the radioactivity was removed from the muscle. Radioactivity was found to have mostly accumulated in the stomach and thyroid. Southern analysis also confirmed rapid degradation of plasmid with only trace detection in muscle at 3 hr post-injection. Despite the fact that injected plasmid can be distributed throughout the entire muscle after intramuscular injection, diffuse through the extracellular matrix, cross the external lamina and enter myofibers distant to the injection site, only 1–2% of muscle fibers are transfected, and are mostly restricted to the injection site. [Levy, M. Y., et al., 1996, *Gene Therapy* 3:201–211; Davis, H. L., et al., 1993, *Hum. Gene Ther.* 4:733–40; Winegar, R. A, et al., *Hum. Gene Therapy*, 7:2185–2194]. Stability of plasmid in the cytoplasm is most likely not a rate-limiting step since plasmid microinjected into the cytoplasm of myotubes will express in up to 70% of the myotubes injected Dowty, M. E., et al., 1995, *Proc. Natl. Acad. Sci.* 92:4572–4576]. Thus, the very low transfection efficiency coupled with the rapid degradation and elimination from the muscle suggests that rapid nuclease degradation is a rate-limiting step for gene transfer of plasmid formulated in saline into muscle cells.

As DNA is taken up by striated skeletal muscle cells certain biological barriers are overcome. These barriers include extracellular nuclease degradation, traversal of the connective tissue of the myofibers and muscle fasciculus (endomysium and perimysium), and traversal of the basal lamina which is composed of three overlapping filamentous networks. Several factors influencing uptake of plasmid by muscle cells have been proposed including uptake by T tubules and caveolae, membrane disruption, uptake by satellite cells which then fuse to myofibers, muscle regeneration, or receptor-mediated uptake.

Gross membrane disruptions occur at the site of injection only, although positive staining for myofibers expressing reporter genes can be observed in myofibers distant to the site of injection [Wolff, J. A., et al., 1992, *J. Cell. Sci.* 103:1249–1259]. This observation is not consistent with membrane disruptions being solely responsible for plasmid uptake. In fact, it has been shown by several investigators that damage to muscle cells prior to or during gene transfer reduces gene expression in muscle [Davis, H. L., et al., 1993, Hum. Gene Ther. 4:151–9; Dowty, M. E., and Wolff, J. A., In: J. A. Wolff (Ed.), Gene Therapeutics: Methods and Applications of Direct Gene Transfer; Birkhauser, Boston, pp. 82–98]. Further, it has been proposed that the ability of cultured muscle cells to take up and express plasmid in vitro provides evidence that membrane disruptions are not needed for uptake of plasmid [Dowty, M. E., and Wolff, J. A., In: J. A. Wolff (Ed.), Gene Therapeutics: Methods and Applications of Direct Gene Transfer; Birkhauser, Boston, pp. 82–98]. If transient membrane disruptions were responsible for allowing plasmid to be taken up, one would expect other colloids such as gold-labeled plasmid, polyethylene glycol, and polyglutamic acid to be taken up via membrane disruption as well. The fact that these colloids are not taken up by muscle cells demonstrates that membrane disruption is not an essential process in gene transfer to muscle [Wolff, J. A., et al., 1992, J. Cell. Sci. 103:1249–1259); Dowty, M. E., and Wolff, J. A., In: J. A. Wolff (Ed.), Gene Therapeutics: Methods and Applications of Direct Gene Transfer; Birkhauser, Boston, pp. 82–98].

It is possible that injected plasmid could be taken up by satellite cells that then fuse with myofibers. However, recent studies suggest that this is not a likely mechanism. Studies by Jiao et al. [Jiao, S., et al., 1992, Hum. Gene Ther. 3:21–33] and Vitadello et al. [Vitadello, M., et al., 1994, Hum. Gene Ther. 5:11–18] have found no positive reporter gene expression in satellite cells in rodents or primates. Also, the lack of enhanced expression early in the regenerative process of muscles pretreated with myotoxic agents that selectively destroy myofibers, not satellite cells, provides further evidence that satellite cells do not contribute to plasmid uptake in striated skeletal muscle.

The T tubule system are imaginations in the sarcolemma that run across a muscle cell. The main function of the T tubules is to communicate with the extracellular space through a series of nerve impulses which are rapidly spread to the interior of the cell. The caveolae have been shown to take up small molecules through potocytosis [Anderson, R. G. W., et al., 1992, Science 255:410–411]. After intramuscular injection, plasmid has been found to a great extent in the T tubules and caveolae. Wolff et al. [Wolff, J. A., et al., 1992, J. Cell. Sci. 103:1249–1259] demonstrated that gold particles complexed with plasmid entered T tubules and caveolae while gold particles complexed with PLL, PEG, or polyglutamate remained largely outside the myofibers. Plasmid which enters the T tubules or caveolae is not able to be washed out from unfixed sections, while dextran, which has similar distribution as plasmid, was removed by multiple washings. The presence of plasmid in the T tubules and caveolae suggest that these structures may play a role in the uptake of plasmid into myofibers. These data also suggest that an active uptake mechanism for plasmid may exist within the T tubules and caveolae.

Hagstrom et al. reported that three DNA binding proteins from the sacroplasmic reticulum (95 kDa, 60 kDa, and 28 kDa) may mediate the uptake and expression of plasmid by striated muscle [Hagstrom, J. E., et al., 1996, Biochem. Mol. Med. 58:113–121]. These proteins bound double-stranded DNA with high affinity. The 95 kDa binding protein was identified as triadin, a skeletal muscle specific protein. The 60 kDa binding protein was suggested to be a proteolytic fragment of triadin. Triadin may be a component of the excitation-contraction coupling machinery in skeletal muscle. The DNA binding proteins in sarcoplasmic reticulum, along with a high concentration of divalent cations within the triads could facilitate the uptake of plasmid. The existence of a specific uptake mechanism is supported by the fact that an excess of salmon sperm DNA, dextran sulfate, heparin, or non-radioactive double-stranded DNA inhibited 32-Phosphorous-DNA binding to the three proteins. Also, proteins that bind double-stranded DNA typically bind dextran sulfate or heparin [Hagstrom, J. E., et al., 1996, Biochem. Mol. Med. 58:113–121; Levy, M. Y., et al., 1996, Gene Therapy 3:201–211].

Hagstrom et al. proposed a model that plasmid binding proteins within sarcoplasmic reticulum and in the presence of a high concentration of divalent cations, facilitate the traversal of plasmid via an intermembrane pore. This model is consistent with the observations that the process of plasmid uptake is saturable and can be reduced via competition with polyanionic molecules [Hagstrom, J. E., et al., 1996, Biochem. Mol. Med. 58:113–121; Levy, M. Y., et al., 1996, Gene Therapy3:201–211]. Likewise, the injection of plasmid containing EDTA (a $Ca^{2+}$ chelator) has been shown to reduce gene expression [Manthorpe, M., et al., 1993, Hum. Gene Ther. 4:419–31; Wolff, J. A., et al., 1991, BioTechniques 11:474–85].

It has been reported that pre-treating muscles with myotoxic agents prior to the injection of plasmid results in improved gene transfer. The two most commonly used myotoxic agents are bupivacaine, which is a local anesthetic, and cardiotoxin, from the venom of the Naja nigricollis snake. Pre-treatment of 0.5%–7.5% bupivacaine 5–7 days prior to the injection of plasmid has been shown to result in a 4–80 fold enhancement of gene expression in mice and rat. Pre-treatment of 10 mM cardiotoxin has been shown to result in a 2–10 fold enhancement of gene expression. Injection of plasmid soon after (i.e., <3 days) the pre-treatment with myotoxic agents resulted in marked lower levels of gene expression. Bupivacaine and cardiotoxin are known to selectively destroy myofibers which then regenerate [Benoit, P. W., and Belt W. D., 1970, J. Anat. 107:547–556; Hall-Craggs, E. C. B., 1980, Br. J. Exp. Pathol. 61:139–149; Akiyama C, et al., 1992, Acta Neuropathol. 83:584–589; Carlson, B. M., et al., 1990, J. Orthopaed. Res. 8:485–494]. The process of regeneration involves revascularization, cellular infiltration, phagocytosis of necrotic damaged muscle, satellite cell proliferation and their fusion into myotubes, and re-innervation [82–84]. With both bupivacaine and cardiotoxin, muscle satellite cells (stem cells), vascular endothelial cells, or the extracellular matrix are spared from damage [68]. The necrosis caused by these myotoxic agents is due to elevated intracellular calcium levels and also from activation of complement [70, 82–85]. High levels of intracellular calcium inhibits normal processes of mitochondria, activates calcium dependent proteases, and saturates the uptake capacity of the sarcoplasmic reticulum, among others [85]. The activation of complement has been shown to initiate the production of C5b-9 membrane attack complex which results in cell lysis. Complement activation also serves as strong chemotactic and stimulating signals to macrophages which efficiently remove necrotic tissue [86]. Myonecrosis occurs about two days after bupivicaine treatment and is characterized by infiltration of polymorphonuclear leukocytes and macrophages [69]. Stem cell proliferation and myotube formation occur within 1–3 days later. Muscle regeneration, or myoregeneration, occurs within 1–2 weeks after the injection of both myotoxic agents. There is no long term muscle damage and complete muscle recovery occurs within 2 weeks after bupivicaine exposure.

Mechanistic studies of plasmid uptake into muscle cells after pre-treatment of the muscle with myotoxic agents are complicated due to the presence of macrophages during the regeneration process. Interestingly, positive staining for reporter genes has only been observed in regenerating myofibers and not in other cell types [Vitadello, M., et al., 1994, Hum. Gene Ther. 5:11–18]. Several mechanisms have been proposed for the enhancement of gene expression in regenerating muscles. It is been proposed that the connective tissue may be less of a barrier to plasmid in regenerating muscle as compared to normal muscle [Davis, H. L., et al., 1993, Hum. Gene Ther. 4:151–9]. Regenerating muscle may allow better diffusion of plasmid due to the smaller diameter of the myofibers and loss of structure of the connective tissue. Whereas mature muscle fibers posses a thick basal lamina which may serve as a physical barrier, regenerating muscle fibers and newly formed myotubes lack the basal lamina.

The findings using myotoxic agents in muscle may have important implications for the use of plasmid-based gene therapy to treat Duchenne muscular dystrophy since regenerating fibers are numerous in the early stages of the disease.

II. Secretion of Expressed Therapeutic Proteins into the Circulation

The secretion of erythropoietin (Epo), rat kallikrein-binding protein (RKBP), human-α-1-antitrypsin (hAAT), human factor IX (hFIX), and human apolipoprotein-E I (apo-E) into the systemic circulation has been reported after intramuscular injection of plasmid formulated in saline. Kuwahara-Rundell, A. Y., et al., 1994, J. Cell. Biochem. Suppl. 18A:233; Miller, G., et al., 1994, Gene Ther. 1, Suppl.2:S16; Tripathy, S. K., et al., Proc. Natl. Acad. Sci. 93:10876–10880; Levy, M. Y., et al., 1996, Gene Therapy 3:201–211; Fazio, V. M., et al., 1994, Biochem. Biophys. Res. Commun. 200:298–305]. Tripathy et al. utilized a mouse erythropoietin (mEpo) expression plasmid that contained a eukaryotic expression cassette controlled by the cytomegalovirus (CMV) early promoter and a bovine growth hormone polyadenylation signal [Tripathy, S. K., et al., Proc. Natl. Acad. Sci. 93:10876–10880]. A single muscle injection of 10 μg of this plasmid in mice increased hematocrits from 48% to 64% at 45 days post-injection. Injections of 100 or 300 μg of the plasmid increased hematocrits to levels of 79% at 45 days post-injection and 67% at 90 days post-injection. mEpo levels in mouse serum at 90 days post-injection were approximately 55 mU/mL. These increases in hematocrits and levels of Epo in serum after single intramuscular injection of plasmid are very comparable to those values observed after transducing and implanting myoblasts in the tibialis anterior muscles of immunocompetent mice [Naffakh, N., et al., 1994, Hum. Gen. Ther. 7:11–21]. However, the extrapolated dose of the mEpo expression plasmid thought needed to produce a significant increase in the hematocrits of humans is 28 mg. This high dose of plasmid may prohibit future testing in humans unless the dose can be lowered either by an improved expression plasmid or delivery system, or by their combination.

III. Nucleic Acid Vaccines

Nucleic acid vaccines, or the use of plasmid encoding antigens, has become an area of intensive research and development in the last half decade. Comprehensive reviews on nucleic acid vaccines have recently been published [M. A. Liu, et al.(Eds.), 1995, DNA Vaccines: A new era in vaccinology, Vol. 772, Ann. NY. Acad. Sci., New York; Kumar, V., and Sercarz, E., 1996, Nat. Med. 2:857–859; Ulmer, J. B., et al., (Eds.) Current Opinion in Immunology; 8:531–536. Vol. 772, Ann. NY. Acad. Sci., New York]. Protective immunity in an animal model using plasmid encoding a viral protein was first observed in 1993 by Ulmer et al. [Ulmer, J. B., et al., 1993, Science 259:1745–1749]. Since then, several studies have demonstrated protective immunity for several disease targets and human clinical trials have been started. Many disease targets have been investigated. Potentially, nucleic acid vaccines may be an attractive alternative vaccination strategy to subunit vaccines, purified viral protein vaccines, or viral vector vaccines. Each of the traditional approaches has limitations that could be overcome if the antigen(s) were expressed directly in cells of the body. Further, these traditional vaccines are only protective in a strain-specific fashion. Thus, it is very difficult, and often impossible using traditional vaccine approaches to obtain long lasting immunity to viruses that have several sera types or viruses that are prone to mutation.

Nucleic acid vaccines offer the potential to produce long lasting immunity against viral epitopes that are highly conserved, such as with the nucleoprotein of viruses. The intramuscular injection of plasmid encoding antigens has been the most investigated route of administration. Transfection of muscle cells with plasmid encoding for antigens has been shown to induce specific and neutralizing antibodies and strong cytotoxic T lymphocyte (CTL) responses. While several other routes of administration have been shown to induce CTLs, only the intramuscular route has been demonstrated to induce protection from a cross-strain lethal challenge with influenza virus [Donnelly, J. J., et al., 1994, J. Immunol. Meth. 176:145–152].

The mechanism for the strong CTL response observed in muscle remains unknown, but it has been suggested to result from the transfer of expressed antigen from muscle cells to non-muscle antigen presenting cells (APCs) [Ulmer, J. B., et al., 1996, Immunology. In Press.; Corr, M., et al., 1996, J. Exp. Med. 184:1555–1560; Doe, B., et al., 1996, Proc. Natl. Acad. Sci. 93, 8578–8583]. Ulmer et al. have proposed that the efficacy of nucleic acid vaccines could be further enhanced by one of at least three methods [Ulmer, J. B., et al., 1996, Current Opinion in Immunology, 8,531–536]: i) the use of delivery systems to increase the stability and distribution of plasmid within the muscle, ii) by the expression (or delivery) of molecules to stimulate antigen presentation/transfer, or iii) by the use of adjuvants that may modulate the immune response.

The use of myotoxic agents, especially bupivacaine, prior to or during the administration of a plasmid expressing an antigen has been utilized to increase the level of gene expression, or possibly to induce damage resulting in the infiltration of polymorphonuclear leukocytes and macrophages. Infiltration of these cells, and specifically antigen presenting cells, may have profound implications for the use of myotoxic agents for plasmid-based vaccines.

IV. Polymeric and Non-polymeric Formulations for Plasmid Delivery to Muscle

As mentioned, plasmid formulated in saline has poor bioavailability in muscle due to rapid degradation of plasmid by extracellular nucleases. One possible approach to overcome the poor bioavailability is to protect plasmid from rapid nuclease degradation by condensing the plasmid with commonly used cationic complexing agents. However, due to the physiology of the muscle, the use of rigid condensed particles containing plasmid for efficient transfection of a larger number of muscle cells has not been successful to date. Cationic lipid and polylysine plasmid complexes do not cross the external lamina to gain access to the caveolae and T tubules [Wolff, J. A., et al., 1992, *J. Cell. Sci.* 103:1249–1259].

Thus, the strategy identified for increasing the bioavailability of plasmid in muscle was to: (i) protect plasmid from rapid extracellular nuclease degradation, (ii) disperse and retain intact plasmid in the muscle, and (iii) facilitate the uptake of plasmid by muscle cells. Two specific methods of accomplishing this is (1) the use of sustained release systems, e.g., polymeric systems and (2) the use of protective, interactive, non-condensing (PINC) systems.

A. Exemplary Polymeric Sustained Release Systems

Due to the rapid rate at which plasmid formulated in saline is degraded and/or removed from the site of injection, one strategy is to develop systems with increased viscosity designed to retain plasmid at the site of injection. Further, since the uptake of plasmid appeared to be a saturable process, maintaining a high concentration of plasmid in muscle for a prolonged period of time may enhance plasmid bioavailability in muscle [March, K. L., et al., 1995, *Hum. Gene Ther.* 6:41–53; Mathiowitz, E., et al., (Sep. 21, 1995), Polymeric gene delivery systems WO 95/24929].

Initial approaches focused on the use of viscous polymeric systems or thermo-gelling systems such as poloxamers. March et al. have reported that Poloxamer 407 was able to increase the apparent transduction rate of adenovirus to vascular smooth muscle cells by greater than 10-fold presumably by maintaining a high pericellular concentration of the adenovirus [March, K. L., et al., 1995, *Hum. Gene Ther.* 6:41–53]. However, we found in several studies that the expression of a reporter gene at 7–8 days was significantly reduced if plasmid was formulated with increasing concentrations of polymers such as PVP, polyethylene glycol, dextran, and carboxymethyl cellulose [Mumper, R. J., et al., 1996, *Pharm. Res.* 13:701–709]. Likewise, a similar result was observed when plasmid was formulated in an unprotective sustained release formulation composed of 20% Poloxamer 407. Although slow release of plasmid can be achieved with this viscous delivery system, the plasmid is not protected from nuclease degradation.

Sodium carboxymethylcellulose is a long chain cellulose ether polymer. Many types are commercially available, varying as to molecular weight (degree of polymerization) and percent carboxymethyl esterification per 10 cellulose units (degree of substitution). When mixed with water the polymers form viscous solutions which possess unique rheological characteristics. Polymerized types of cellulose ethers exhibit pseudoplastic and thixotropic behavior. By thixotropic behavior is meant that the long-chain molecules tend to orient themselves in the direction of flow; as the applied force is increased, the resistance to flow is decreased. Yet when high shear stress is removed, the solution will quickly revert to its original viscous state. Some celluloses exhibit thixotropic behavior wherein the solution returns to its viscous state over a period of time. The pseudoplasticity and thixotropic properties of sodium carboxymethylcellulose can be utilized for intramuscular injection of nucleic acid, such as plasmid DNA. A formulation of the viscous solution of sodium carboxymethylcellulose in isotonic saline containing plasmid DNA becomes fluid due to the pressure of injection by a syringe and needle then thicken once deposited in the muscle. The thickening of the injected formulation in situ provides retention of the expression vector within the muscle resulting in a controlled and sustained release and an enhanced uptake of the vector by the muscle cells.

In an alternative embodiment a thermoreversible gel may be used. After i.m. administration, plasmid DNA is maintained within the muscle by using a thermo-reversible gel formulation. The use of compounds that are aqueous at ambient temperature, yet are gels at body temperatures (e.g. 37° C. for humans) are used to ease the formulation and administration of the DNA, yet transition to and maintain the gel state for increased bio-availability at temperatures encountered in vivo.

Such formulations (thermo-reversible gels) are prepared by adjusting the concentrations of polymers in aqueous solutions so that the vector delivery system will be liquid at room temperature or below and will be in the form of a gel in situ in the muscle at physiologic temperatures. Poloxamers (Pluronic F127®, Poloxamer 407®), poloxamines and the concentration of the polymers may be adjusted according to the formulation depending upon the route of administration (i.e., topical, i.m.,) for nucleic acid or nucleic acid complexes. These adjustments may be found in U.S. Pat. No. 5,292,516 which is incorporated by reference herein.

B. Protective, Interactive, Non-condensing (PINC) Systems

Delivery and expression of nucleic acids in many formulations is limited due to degradation of the nucleic acids by components of organisms, such as nucleases. Thus, protection of the nucleic acids when delivered in vivo can greatly enhance the resulting expression, thereby enhancing a desired pharmacological or therapeutic effect. It was found that certain types of compounds which interact with a nucleic acid (e.g., DNA) in solution but do not condense the nucleic acid provide in vivo protection to the nucleic acid, and correspondingly enhance the expression of an encoded gene product.

We have described the use of delivery systems designed to interact with plasmids and protect plasmids from rapid extracellular nuclease degradation [Mumper, R. J., et al., 1996, *Pharm. Res.* 13:701–709; Mumper, R. J., et al., 1997. Submitted to *Gene Therapy*]. A characteristic of the PINC systems is that they are non-condensing systems that allow the plasmid to maintain flexibility and diffuse freely throughout the muscle while being protected from nuclease degradation.

A common structural component of the PINC systems is that they are amphiphilic molecules, having both a hydrophilic and a hydrophobic portion. The hydrophilic portion of the PINC is meant to interact with plasmids by hydrogen bonding (via hydrogen bond acceptor or donor groups), Van der Waals interactions, or/and by ionic interactions. For example, PVP and N-methyl-2-pyrrolidone (NM2P) are hydrogen bond acceptors while PVA and PG are hydrogen bond donors.

All four molecules have been reported to form complexes with various (poly)anionic molecules [Buhler V., BASF Aktiengescellschaft Feinchemie, Ludwigshafen, pp 39–42; Galaev Y, et al., *J. Chrom. A*. 684:45–54 (1994); Tarantino R. et al. *J. Pharm. Sci*. 83:1213–1216 (1994); Zia, H., et al., *Pharm. Res.* 8:502–504 (1991);]. The hydrophobic portion of the PINC systems is designed to result in a coating on the plasmid rendering its surface more hydrophobic. Kabanov et al. have described previously the use of cationic polyvinyl derivatives for plasmid condensation designed to increase plasmid hydrophobicity, protect plasmid from nuclease degradation, and increase its affinity for biological membranes [Kabanov, A. V., and Kabanov, V. A., 1995, *Bioconj. Chem.* 6:7–20; Kabanov, A. V., et al., 1991, *Biopolymers* 31:1437–1443; Yaroslavov, A. A., et al., 1996, *FEBS Letters* 384:177–180].

Substantial protective effect is observed; up to at least a one log enhancement of gene expression in rat muscle over plasmid formulated in saline has been demonstrated with these exemplary PINC systems. We have also found that the expression of reporter genes in muscle using plasmids complexed with the PINC systems was more reproducible than when the plasmid was formulated in saline. For example,. the coefficient of variation for reporter gene expression in muscle using plasmid formulated in saline was 96+35% (n=20 studies; 8–12 muscles/study) whereas with coefficient of variation with plasmids complexed with PINC systems was 40±19% (n=30 studies; 8–12 muscles/study). The high coefficient of variation for reporter gene expression with plasmid formulated in saline has been described previously [Davis, H. L., et al., 1993, *Hum. Gene Ther.* 4:151–9]. In addition, in contrast with the results for DNA:saline, there was no significant difference in gene expression in muscle when plasmid with different topologies were complexed with polyvinyl pyrrolidone (PVP). This suggests that PVP is able to protect all forms of the plasmid from rapid nuclease degradation.

1. Summary of Interactions Between a PINC Polymer (PVP) and Plasmid

We have demonstrated using molecular modeling that an exemplary PINC polymer, PVP, forms hydrogen bonds with the base pairs of a plasmid within its major groove and results in a hydrophobic surface on the plasmid due to the vinyl backbone of PVP. These interactions are supported by the modulation of plasmid zeta potential by PVP as well as by the inhibition of ethidium bromide intercalation into complexed plasmid. We have correlated apparent binding between PVP and plasmid to pH and salt concentration and have demonstrated the effect of these parameters on β-gal expression after intramuscular injection of plasmid/PVP complexes [Mumper, R. J., et al., 1997. Submitted to *Gene Therapy*]. A summary of the physico-chemical properties of plasmid/PVP complexes is listed in Table 2 below.

In comparison, immunoreactivity for β-gal was observed in a wide area of muscle tissue after intramuscular injection of CMV-β-gal plasmid/PVP complex (1:17 w/w) in 150 mM NaCl. It appeared that the majority of positive muscle fibers were located at the edge of muscle bundles. Thus, staining for β-gal in rat muscle demonstrated that, using a plasmid/PVP complex, the number of muscle fibers stained positive for β-gal was approximately 8-fold greater than found using a saline formulation. Positively stained muscle fibers were also observed over a much larger area in the muscle tissue using the plasmid/PVP complex providing evidence that the injected plasmid was widely dispersed after intramuscular injection.

We conclude that the enhanced plasmid distribution and expression in rat skeletal muscle was a result of both protection from extracellular nuclease degradation due to complexation and hyper-osmotic effects of the plasmid/PVP complex. However, Dowty and Wolff et al. have demonstrated that osmolarity, up to twice physiologic osmolarity, did not significantly effect gene expression in muscle [Dowty, M. E., and Wolff, J. A. In: J. A. Wolff (Ed.), 1994, *Gene Therapeutics: Methods and Applications of Direct Gene Transfer*. Birkhauser, Boston, pp. 82–98]. This suggests that the enhanced expression of plasmid due to PVP complexation is most likely due to nuclease protection and less to osmotic effects. Further, the surface modification of plasmids by PVP (e.g., increased hydrophobicity and decreased negative surface charge) may also facilitate the uptake of plasmids by muscle cells.

3. Structure-activity Relationship of PINC Polymers

We have found a linear relationship between the structure of a series of co-polymers of vinyl pyrrolidone and vinyl acetate and the levels of gene expression in rat muscle. We have found that the substitution of some vinyl pyrrolidone monomers with vinyl acetate monomers in PVP resulted in a co-polymer with reduced ability to form hydrogen bonds with plasmids. The reduced interaction subsequently led to

TABLE 2

Summary of the Physico-Chemical Properties of Plasmid/PVP Complexes [46–47]

| Method | Result |
|---|---|
| Molecular modeling | Hydrogen bonding and hydrophobic plasmid surface observed |
| Fourier-transformed Infra-red | Hydrogen bonding demonstrated |
| DNase 1 challenge | Decreased rate of plasmid degradation in the presence of PVP |
| Microtitration Calorimetry | Positive heats of reaction indicative of an endothermic process |
| Potentiometric titration | One unit pH drop when plasmid and PVP are complexed |
| Dynamic Dialysis | Rate of diffusion of PVP reduced in the presence of plasmid |
| Zeta potential modulation | Surface charge of plasmid decreased by PVP |
| Ethidium bromide Intercalation complexation | Ethidium bromide intercalation reduced by plasmid/PVP |
| Osmotic pressure | Hyper-osmotic formulation (i.e., 340 mOsm/kg $H_2O$) |
| Luminescence Spectroscopy | Plasmid/PVP binding decreased in salt and/or at pH 7 |

2. Histology of Expression in Muscle

Immunohistochemistry for β-gal using a slide scanning technology has revealed the uniform distribution of β-gal expression sites across the whole cross-sections of rat tibialis muscles. Very localized areas were stained positive for β-gal when CMV-β-gal plasmid was formulated in saline. β-gal positive cells were observed exclusively around the needle tract when plasmid was injected in saline. This is in agreement with previously published results [Wolff, J. A., et al., 1990, *Science* 247:1465–68; Davis, H. L., et al., 1993, *Hum. Gene Ther.* 4:151–9; Davis, H. L., et al., 1993, *Hum. Gene Ther.* 4:733–40].

decreased levels of gene expression in rat muscle after intramuscular injection. The expression of β-gal decreased linearly (R=0.97) as the extent of vinyl pyrrolidone monomer (VPM) content in the co-polymers decreased.

These data demonstrate that pH and viscosity are not the most important parameters effecting delivery of plasmid to muscle cells since these values were equivalent for all complexes. These data suggest that enhanced binding of the PINC polymers to plasmid results in increased protection and bioavailability of plasmid in muscle.

4. Additional PINC Systems

The structure-activity relationship described above can be used to design novel co-polymers that will also have enhanced interaction with plasmids. It is expected that there is "an interactive window of opportunity" whereby enhanced binding affinity of the PINC systems will result in a further enhancement of gene expression after their intramuscular injection due to more extensive protection of plasmids from nuclease degradation. It is expected that there will be an optimal interaction beyond which either condensation of plasmids will occur or "triplex" type formation, either of which can result in decreased bioavailability in muscle and consequently reduced gene expression.

As indicated above, the PINC compounds are generally amphiphilic compounds having both a hydrophobic portion and a hydrophilic portion. In many cases the hydrophilic portion is provided by a polar group. It is recognized in the art that such polar groups can be provided by groups such as, but not limited to, pyrrolidone, alcohol, acetate, amine or heterocyclic groups such as those shown on pp. 2–73 and 2–74 of CRC Handbook of Chemistry and Physics (72nd Edition), David R. Lide, editor, including pyrroles, pyrazoles, imidazoles, triazoles, dithiols, oxazoles, (iso)thiazoles, oxadiazoles, oxatriazoles, diaoxazoles, oxathioles, pyrones, dioxins, pyridines, pyridazines, pyrimidines, pyrazines, piperazines, (iso)oxazines, indoles, indazoles, carpazoles, and purines and derivatives of these groups, hereby incorporated by reference.

Compounds also contain hydrophobic groups which, in the case of a polymer, are typically contained in the backbone of the molecule, but which may also be part of a non-polymeric molecule. Examples of such hydrophobic backbone groups include, but are not limited to, vinyls, ethyls, acrylates, acrylamides, esters, celluloses, amides, hydrides, ethers, carbonates, phosphazenes, sulfones, propylenes, and derivatives of these groups. The polarity characteristics of various groups are quite well known to those skilled in the art as illustrated, for example, by discussions of polarity in any introductory organic chemistry textbook.

The ability of such molecules to interact with nucleic acids is also understood by those skilled in the art, and can be predicted by the use of computer programs which model such intermolecular interactions. Alternatively or in addition to such modeling, effective compounds can readily be identified using one or more of such tests as 1) determination of inhibition of the rate of nuclease digestion, 2) alteration of the zeta potential of the DNA, which indicates coating of DNA, 3) or inhibition of the ability of intercalating agents, such as ethidium bromide to intercalate with DNA.

V. Diseases and Conditions for Intramuscular Plasmid Delivery

The formulations described herein can be utilized for the delivery and expression of many different coding sequences. In particular, the demonstrated effectiveness for the PINC systems for delivery to muscle indicate that such formulations are effective for delivery of a large variety of coding sequences to muscle. Specific suggestions for delivery of coding sequences to muscle include those summarized in Table 3 below.

TABLE 3

Proposed Applications for Plasmid-Based Gene Therapy by Intramuscular Injection

| Muscle and nerve disorders | Selected References |
|---|---|
| Duchenne's muscular dystrophy | Acsadi 1991 [5], Karpati 1993 [6], Miller 1995 [7] |
| Myotrophic disorders (IGF-1) | Coleman 1997 [8], Alila 1997 [9] |
| Neurotrophic disorders (IGF-1) | Alila 1997 [9], Rabinovsky 1997 [10] |
| Secretion of expressed protein into the systemic circulation | |
| | |
| Hemophilias A and B | Anwer 1996 [11], Kuwahara-Rundell 1994 [12], Miller 1994 [13] |
| Erythropoietin-responsive | Tripathy 1996 [14] |
| Pituitary dwarfism | Anwer 1996 [11], Dahler 1994 [15] |
| α1-Antitrypsin deficiency | Levy 1996 [16] |
| Autoimmune and Inflammatory diseases | Raz 1993 [17] |
| Hypercholesterolema | Fazio 1994 [18] |
| Hypotension | Ma 1995 [19] |
| Hypertension | Xiong 1995 [20] |
| Nucleic acid vaccines | |
| | |
| Herpes Simplex Virus | Manickan 1995 [21], Ghiasi 1995 [22], McClements 1996 [23], Kriesel 1996 [24] |
| Hepatitis B Virus | Davis 1993 [25], Davis 1994 [26], Davis 1996 [27] |
| Influenza Virus | Donnelly 1995 [28], Ulmer 1993 [29], Ulmer 1994 [30] |
| Tuberculosis | Lowrie 1994 [31], Tascon, 1996 [32] |
| Human Immunodeficiency Virus | Shiver 1995 [33], Coney 1994 [34], Wang 1993 [35] |
| Cancer | Raz 1993 [17], Russell 1994 [36] |
| Maleria | Hoffman 1995 [37], Sedegah 1994 [38] |
| Hepatitis C virus | Major 1995 [39], Lagging 1995 [40] |
| Flavivirus | Phillpotts 1996 [41] |
| Cytomegalovirus | Pande 1995 [42] |
| Salmonella typhi | Lopez-Macias 1995 [43] |
| Mycoplasma pulmonis | Lai 1995 [44] |
| Rabies virus | Xiang 1995 [45] |

VI. Targeted Delivery of Nucleic Acid/PINC/Targeting Ligand Complex

In addition to the nucleic acid/PINC complexes described above for delivery and expression of nucleic acid sequences, in particular embodiments it is also useful to provide a targeting ligand in order to preferentially obtain expression in particular tissues, cells, or cellular regions or compartments.

Such a targeted PINC complex includes a PINC system (monomeric or polymeric PINC compound) complexed to plasmid (or other nucleic acid molecule). The PINC system is covalently or non-covalently attached to (bound to) a targeting ligand (TL) which binds to receptors having an affinity for the ligand. Such receptors may be on the surface or within compartments of a cell. Such targeting provides enhanced uptake or intracellular trafficking of the nucleic acid.

The targeting ligand may include, but is not limited to, galactosyl residues, fucosal residues, mannosyl residues, carnitine derivatives, monoclonal antibodies, polyclonal antibodies, peptide ligands, and DNA-binding proteins. Examples of cells which may usefully be targeted include, but are not limited to, antigen-presenting cells, hepatocytes, myocytes, epithelial cells, endothelial cells, and cancer cells.

Formation of such a targeted complex is illustrated by the following example of covalently attached targeting ligand (TL) to PINC system:

TL-PINC +Plasmid→TL-PINC::::::Plasmid

Formation of such a targeted complex is also illustrated by the following example of non-covalently attached targeting ligand (TL) to PINC system TL::::::PINC+Plasmid→TL::::::PINC::::::Plasmid or alternatively, PINC+Plasmid→PINC::::::::Plasmid+ TL→TL::::::PINC::::::Plasmid In these examples :::::::: is non-covalent interaction such as ionic, hydrogen-bonding, Van der Waals interaction, hydrophobic interaction, or combinations of such interactions.

A targeting method for cytotoxic agents is described in Subramanian et al., International Application No. PCT/US96/08852, International Publication No. WO 96/39124, hereby incorporated by reference. This application describes the use of polymer affinity systems for targeting cytotoxic materials using a two-step targeting method involving zip polymers, i.e., pairs of interacting polymers. An antibody attached to one of the interacting polymers binds to a cellular target. That polymer then acts as a target for a second polymer attached to a cytotoxic agent. As referenced in Subramanian et al., other two-step (or multi-step) systems for delivery of toxic agents are also described.

In another aspect, nucleic acid coding sequences can be delivered and expressed using a two-step targeting approach involving a non-natural target for a PINC system or PINC-targeting ligand complex. Thus, for example, a PINC-plasmid complex can target a binding pair member which is itself attached to a ligand which binds to a cellular target (e.g., a MAB). Binding pairs for certain of the compounds identified herein as PINC compounds as identified in Subramanian et al. Alternatively, the PINC can be complexed to a targeting ligand, such as an antibody. That antibody can be targeted to a non-natural target which binds to, for example to a second antibody of the compounds identified herein as PINC compounds as identified in Subramanian et al. Alternatively, the PINC can be complexed to a tareting ligand, such as an antibody. That antibody can be targeted to a non-natural target which binds to, for example to a second antibody The following examples are offered by way of illustration and are not intended to limit the scope of the invention in any manner.

EXAMPLE 1

Demonstration of PVP Plasmid DNA Complex Formation

A given amount of lyophilized plasmid DNA is rehydrated with water and made isotonic with sterile 5M NaCl. After complete rehydration, an appropriate volume of sterile stock PVP solution in water is added to result in the desired final PVP concentration in isotonic saline. Alternatively, if plasmid DNA is already in solution, the appropriate volumes of plasmid DNA, 5M NaCl and stock PVP solutions are added to result in the desired proportions.

The complex is allowed to form at 25° C. after gentle shaking. For example:

| Ingredient | Amount |
| --- | --- |
| lyophilized DNA | 1 mg |
| sterile water | 0.770 ml |
| 25% PVP in water | 0.2 ml |
| 5M NaCl | 0.030 ml |

Final formulation: 1 mg of DNA/1 ml of 5% PVP in isotonic saline.

A dynamic dialysis experiment with three complexes was undertaken to determine the retention of PVP (MW=10 kDa) within dialysis sacs. Spectra/Por CE (cellulose ester) membranes with a MW cut-off of 25 kDa were employed. Three 1 ml formulations and corresponding controls were placed in pre-washed sacs, the sacs were closed and suspended in 100 ml saline at 25° C. The formulations and controls were as follows:

| | PVP/DNA (w/w) |
| --- | --- |
| Formulations | |
| 90 mg PVP and 0.5 mg CMV-β-gal in saline | 180:1 |
| 60 mg PVP and 0.5 mg CMV-β-gal in saline | 120:1 |
| 30 mg PVP and 0.5 mg CMV-β-gal in saline | 60:1 |
| Controls | |
| 90 mg PVP and 0.5 mg CMV-β-gal in saline | 180:0 |
| 60 mg PVP and 0.5 mg CMV-β-gal in saline | 120:0 |
| 30 mg PVP and 0.5 mg CMV-β-gal in saline | 60:0 |
| 0.5 mg CMV-β-gal in saline | 0:1 |

Aliquots were taken over 24 hours. The results are shown in FIG. 1. The fraction of PVP remaining in the dialysis sac was plotted over time. In all cases, the rate of PVP diffusion through the dialysis membrane was decreased in the presence of plasmid DNA, indicating complex formation between PVP and plasmid DNA at the three weight ratios tested. It was also determined that the sac volume remained constant during the duration of the experiment and that adherence of PVP to the membrane was negligible.

EXAMPLE 2

Demonstration of Increased Transfection Efficiency With Amphiphilic Polymers

It was demonstrated that amphiphilic polymers such as PVP (MW=50 kDa), PEG (MW=8 kDa), and Poloxamer 407® can increase the efficiency of cell transfection, in-vitro in studies carried out using C2C12 myoblasts. Transfections were made using combinations of a complex and various polymers. The plasmid DNA complex consisted of plasmid DNA:condensing agent:Peptide 1 (1:64:3−/+/−) (The condensing agent may be those as are known in the art, for example, dendrimers or polylysine). (Peptide-1 is a lytic peptide. A peptide similar to Peptide 1 is described in U.S. patent application Ser. No. 07/913,669, filed Jul. 14, 1992).

The results show that at higher concentrations, e.g., 7.5% of the amphiphilic polymers PVP; PEG; and Poloxamer, the transfection efficiency of the plasmid DNA complex was significantly enhanced over the plasmid DNA complex alone or the polymers alone. Conversely, with the largely ionic polymer, CMC, the synergistic effect was not observed. This may have been due to destabilization of the net positively charged plasmid DNA complex by the negatively charged CMC.

While not being limited in scope by any theory set forth, several mechanisms of action of amphiphilic polymers may account for the observed results including: Stabilization of plasmid DNA complexes due to coating; increased cell membrane permeability, thereby allowing easier passage of the plasmid DNA complex through the cell; membrane and/or volume exclusion, increasing the concentration of plasmid DNA complexes at the cell surface. Poloxamer 407® has been shown to improve the transduction efficiency of adenoviral vectors by apparently maintaining a high pericellular concentration of the vector or by disrupting the cell membrane. K. March et al. Facilitation of Adenoviral Gene Delivery by Poloxamer 407®. Proceed. Intern. Symp. Control. Rel. Bioact. Mater., 21 (1994).

EXAMPLE 3

Demonstration of Increased Transfection Efficiency Utilizing PEG with a Lytic Peptide $C_2C_{12}$ myoblasts were transfected with 4 um plasmid DNA in 10%, 20%, and 30% PEG (8 kDa) with and without the presence of 6 ug of an endosomal release peptide (lytic peptide) The results are shown in FIG. 3. With no lytic peptide, only at 20% PEG as a carrier did transfection result. 10% and 30% PEG carriers did not give transfection. Additionally, when the lytic peptide was included, the transfection efficiency was enhanced 100-fold for the 20% PEG carrier. This result suggested the importance of a lytic agent in the carrier system, but also that the plasmid DNA in 20% PEG (without the peptide) was probably being taken up by the cell but degraded in the lysosomes. It has been found that 20% PEG is optimal for transfecting Micromonospora with bacteriophage DNA. J L Caso et al. Transfection in Micromonospora. *Appl. Environ. Microbiol.* 1987; 53 (10): 2544–47. The ability of the 20% PEG carrier to transfect cells is attributed to its ability to interact with plasmid DNA. Hydrodynamic light scattering data has shown that 20% PEG but not 10% PEG or 30% PEG can collapse plasmid DNA, presumably due to water exclusion.

EXAMPLE 4

Demonstration of Enhanced Nucleic Acid Uptake and Expression Utilizing PVP

Polyvinylpyrrolidone (PVP) is a polyamide that forms complexes with a wide variety of substances and is chemically and physiologically inert. Applicants have shown that PVP enhances nucleic acid uptake/expression in muscle and should prove useful in delivering nucleic acids for the prophylactic treatment of diseases.

A CMV-β-galactosidase expression vector system was formulated in saline or 5% PVP and administered into the tibialis muscle of a rat. The activity of β-galactosidase gene product was measured in muscle extract at various time intervals after injection.

Delivery of DNA-PVP Formulation into Muscle: 5–6 week old male rats (Fisher 344 strain, 120–130 g) from Harlan Sprague-Dawley laboratories were used. The animals were housed in microisolators at Baylor Animal Facility and maintained on a 12 h/12 h day/night cycle, with room temperature at 72° F., and at 40% humidity. Animals were anesthetized with a mixture of Ketamine (42.8 mg/ml), Xylazine (8.6 mg/ml) and Acepromazine (1.4 mg/ml) at a dose of 0.5–0.7 ml/kg, i.m. A 2–4 mm incision was made aseptically and 50 µl of a DNA formulation in PVP or saline was injected into the tibialis muscle of both legs. At various time intervals after injection, animals were anaesthetized, sacrificed by thoracotomy and the tibialis muscle was harvested and collected on dry ice and stored at −70° C. until assayed for β-galactosidase activity.

Extraction and Measurement of β-Galactosidase Activity in Muscle Injected with DNA-PVP Formulation:

β-galactosidase was extracted with 1.5 ml of Tris-EDTA-NaCl buffer containing the protease inhibitors leupeptin (1 µM), pepstatin (1 µM) and PMSF (0.25 mM). The extract was centrifuged at 13 K rpm for 15 min at 4° C. The supernatant was collected and 100 µg protein was assayed for β-galactosidase activity using a chemiluminescence detection system.

An example of a suitable system is the Galacto-Light™ or Galacto-Light Plus™ available from Tropix, Inc. of Bedford, Massachusetts. Galacto-Light™ and Galacto-Light Plus™ are a chemiluminescent reporter assay systems designed for the rapid, sensitive, and non-isotropic detection of β-galactosidase in cell lysates. The Galacto-Light™ (Galacto-Light Plus™ ) reporter assay incorporates Galacton™ (Galacton-Plus™ chemiluminescent substrate for β-galactosidase with Emerald™ luminescence enhancer. The chemiluminescent assay has a wide dynamic range, enabling detection of 2 fg to 20 ng of β-galactosidase. Jain, V., and I. Magrath. A Chemiluminescent Assay for Quantitation of β-Galactosidase in the Femtogram Range: Application to Quantitation of β-Galactosidase in lacZ-Transfected Cells. *Anal. Biochem.* 199: 119–124 (1991) incorporated herein by reference. Galacton™ chemiluminescent substrate has a half-life of light emission of approximately 4.5 minutes after the addition of Galacto-Light™ accelerator. It is suited for use with luminometers with automatic injectors and other instrumentation in which light emission measurements can be taken within a short period of time. Luminometer measurements taken within a narrow time frame make results more accurate and simple to interpret. Galacton-Plus™ chemiluminescent substrate emits light which persists at a constant level for up to 60 minutes after the addition of Galacto-Light™ accelerator. This substrate is ideal for use with either plate luminometers that do not have automatic injection capabilities or with scintillation counters.

Cell lysate or purified β-galactosidase is incubated with reaction buffer for 15 minutes to 1 hour. Galacton™ (Galacton-Plus™ ) chemiluminescent substrate present in the reaction buffer is cleaved by the enzyme. The sample is then placed in a luminometer chamber and a light emission accelerator is added which terminates the β-galactosidase activity and accelerates light emission. Light output is quantitatively measured using a 5 second integral. It is important to stay within the linear range of the assay, especially if β-galactosidase is being used to normalize transfections. High signals can potentially saturate a photomultiplier tube resulting in artificially low signals. In addition, low signals that approach background levels may also be outside the linear range. In these cases, the amount of cell extract used in the assay should be adjusted to bring the assay within the linear range. The Galacto-Light™ (Galacto-Light Plus™ ) system has been formulated for luminometers with a 300 µl automatic injector. When using Galacto-Light™, manual injection may be performed if luminescence intensities are measured at approximately the same interval after adding the light emission accelerator to each sample. However, Galacto-Light Plus™ eliminates this need due to the long half-life of light emission exhibited by Galacton-Plus™. Reaction components should be scaled down if a luminometer with a smaller volume injector is used, however, sensitivity may be affected slightly. For plate luminometers it will be necessary to scale down the reaction volumes proportionately. However, it is recommended to keep the volume of cell extract between 5 and 2 μ. The lysis solution included with the kit may be substituted with alternative lysis solutions and lysis procedures. This may be desirable if assays for other co-transfected reporters require specific assay buffers. Alternative lysis solutions should be compared with the Galacto-Light™ Lysis Solution to ensure optimal performance of the assay. Chemiluminescent reporter assays may be conducted in cells or tissues that have endogenous β-galactosidase activity. Endogenous enzyme activity is slightly reduced at the pH of the Galacto-Light™ Reaction Buffer, while bacterial β-galactosidase encoded on transfected plasmids is only slightly affected. In this case, it is important to assay the level of endogenous enzyme with non-transfected cell extracts. Significant reductions of endogenous activity can be achieved using heat inactivation. Tissue extracts may also require the use of protease inhibitors.

The following reagents are used: Chemiluminescent Substrate: Galacton™ or Galacton-Plus™ is a 100X concentrate which is diluted in reaction buffer diluent prior to use (store at 4° C. or optimally at −20° C.); Lysis Solution containing 100 mM potassium phosphate pH 7.8, 0.2% Triton X-100 (Store at 4 ° C.). Dithiothrietol (DTT) should be added fresh prior to use to a final concentration of 1 mM; Reaction Buffer Diluent containing 100 mM sodium phosphate pH 8.0, 1 mM magnesium chloride (store at 4° C.); Accelerator contains a ready-to-use luminescence accelerator reagent (store at 4° C.).

Preparation of Cell Extracts From Tissue Culture Cells (1) Aliquot the required amount of Lysis Solution. Add fresh DTT to 1 mM. (2) Rinse cells 2 times with 1× Phosphate Buffered Saline (PBS). (3) Add Lysis Solution to cover the cells (250μl of Lysis Buffer for a 60 mm culture plate should be adequate). (4) Detach cells from culture plate using a rubber policeman or equivalent. Non-adherent cells should be pelleted and lysis buffer should be added sufficient to cover the cells. The cells should then be resuspended in the lysis buffer by pipetting. (5) Transfer cells to a microfuge tube and centrifuge for 2 minutes to pellet any debris. (6) Transfer supernatant to a fresh microfuge tube. Cell extracts may be used immediately or frozen at −70° C. for future use.

Chemiluminescent Detection Procedure

It is recommended that all assays are performed in triplicate. (1) Dilute GalactonT™ (Galacton-Plus™) substrate 100-fold with Galacto-Light™ Reaction Buffer Diluent to make Reaction Buffer. This mixture will remain stable for several months if stored uncontaminated at 4° C. It is recommended to only dilute the amount of substrate that will be used within a two month period. (2) Warm to room temperature the amount of Reaction Buffer required for the entire experiment. (3) Aliquot 2 to 201μl of individual cell extracts into luminometer sample tubes. (The amount of cell extract required may vary depending on the amount of expression and the instrumentation used. Use 5μl of extract for positive controls and 10 to 20 μl of extract for experiments with potentially low levels of enzyme. It is important to vary the concentrations of extract to keep the signal within the linear range of the assay.) (4) Add 200 μl of Reaction Buffer to a luminometer cuvette and gently mix. Incubate at room temperature for 60 minutes. Incubations can be as short as 15 minutes, but the linear range of the assay may decrease. (Measurements are time dependent. Reaction Buffer should be added to sample extracts in the same time frame as they are counted on the luminometer. For example, if it takes 10 seconds to completely count a sample, then Reaction Buffer should be added to tubes every 10 seconds.) (5) Place cuvette in a luminometer. Inject 300μl of Accelerator. After a 2 to 5 second delay following injection, count the sample for 5 seconds. If manual injection is used, then the Accelerator should be added in the same consistent time frame as the Reaction Buffer is added. This is critical when using Galacton™.

Preparation of Controls

Positive Control

Add 1 μl of β-galactosidase (10 units/ml, Sigma Cat. No. G-5635 diluted in 0.1 M sodium phosphate pH 7.0, 1.0% BSA) to mock transfected cell extract equivalent to the volume of experimental cell extract used. Proceed with Chemiluminescent Detection Procedure.

Negative Control

Assay of volume of mock transfected cell extract equivalent to the volume of experimental cell extract used. Proceed with Chemiluminescent Detection Procedure.

Heat Inactivation of Endogenous β-galactosidase Some cell lines may exhibit relatively high levels of endogenous β-galactosidase activity. This may lead to background which will decrease the overall sensitivity of the assay by lowering the signal to noise ratio. A procedure for heat inactivation of endogenous β-galactosidase activity has been described by Young et al. Young, Dorothy C., S. D. Kingsley, K. A. Ryan, and F. J. Dutko. Selective Inactivation of Eukaryotic β-Galactosidase in Assays for Inhibitors of HIV-1 TAT Using Bacterial β-Galactosidase as a Reporter Enzyme. Anal. Biochem. 215:24–30 (1993), incorporated herein by reference. A modified version of this protocol has also been described by Shaper et al. in which a cocktail of protease inhibitors is used in conjunction with the heat inactivation procedure for reducing β-galactosidase in tissue extracts. Shaper, N., Harduin-Lepers, A., and Shaper, H. H. Male Germ Cell Expression of Murine β4-Galactosyltransferase. A 796-base pair genomic region containing two cAMP-responsive elements (CRE)-like elements, mediates expression in transgenic mice. J. Biol. Chem. 269:25165–25171 (1994), incorporated herein by reference.

Inactivation of β-Galactosidase Activity in Cell Extracts

The following procedures should be performed immediately prior to the Chemiluminescent Detection Procedure in the Preparation of Cell Extracts From Tissue Culture Section. (1) Following cell extract preparation, heat the extract to 48° C. for 50 minutes. (2) Proceed with Chemiluminescent Detection Procedure. (Although Young et al. suggest 50° C. for 60 minutes, heat inactivation at 48° C. for 50 minutes is suggested.)

Inactivation of Endogenous β-Galactosidase Activity in Tissue Extracts (1) To the Galacto-Light™ lysis buffer, add PMSF to a final concentration of 0.2 mM and leupeptin to a final concentration of 5 μg/mM just before use. (2) Heat inactivate the extracts by heating at 48° C. for 60 minutes. (3) Proceed with Chemiluminescent Detection Procedure. (AEBSF (Sigma Cat. No. A-5938) may be used in place of PMSF (Sigma Cat. No. P-7626). AEBSF is a water soluble serine protease inhibitor).

Figure 5:
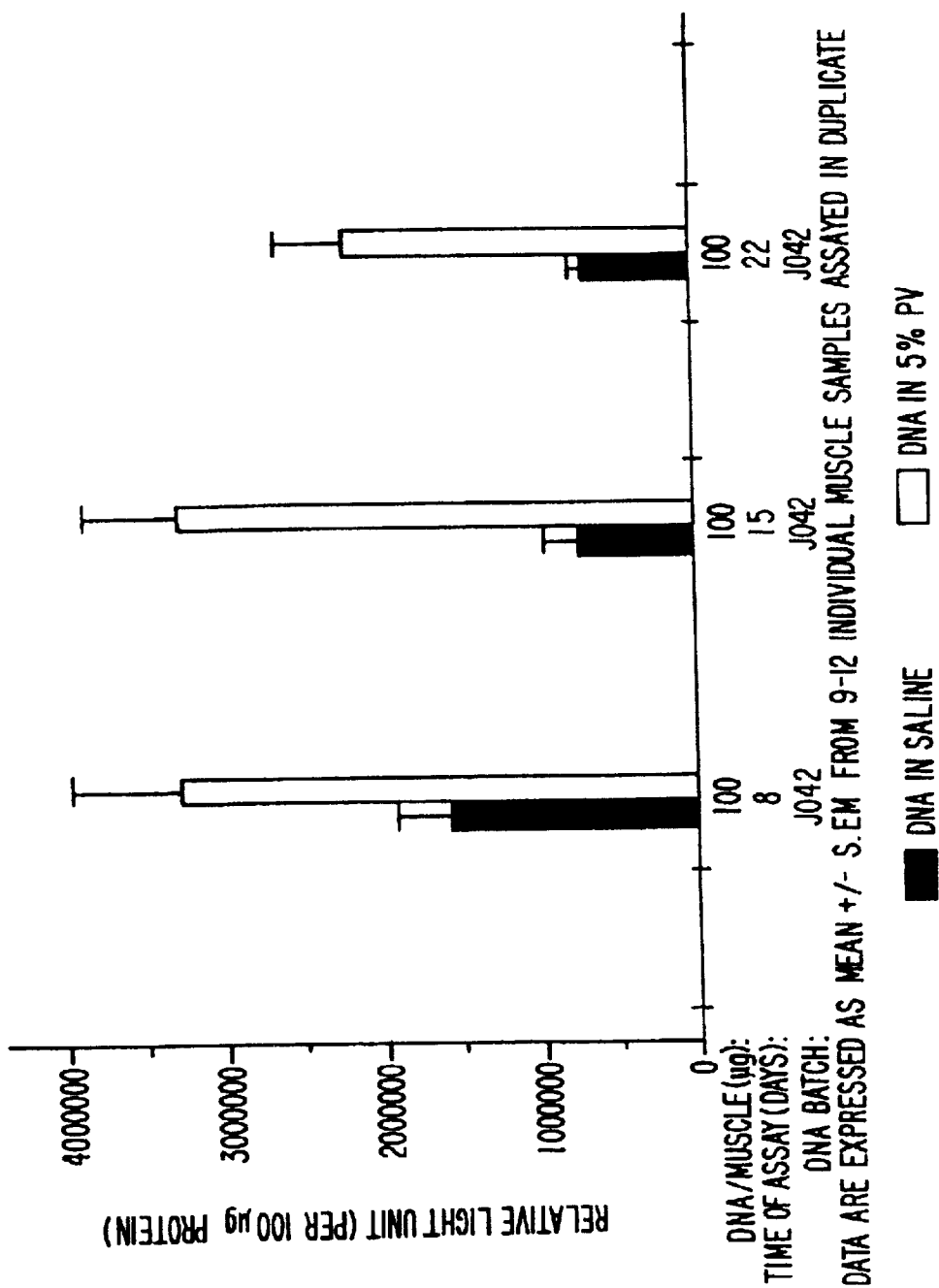
FIG. 5 illustrates the time course of β-galactosidase expression in PVP as compared to the time course in saline.
Figure 6:
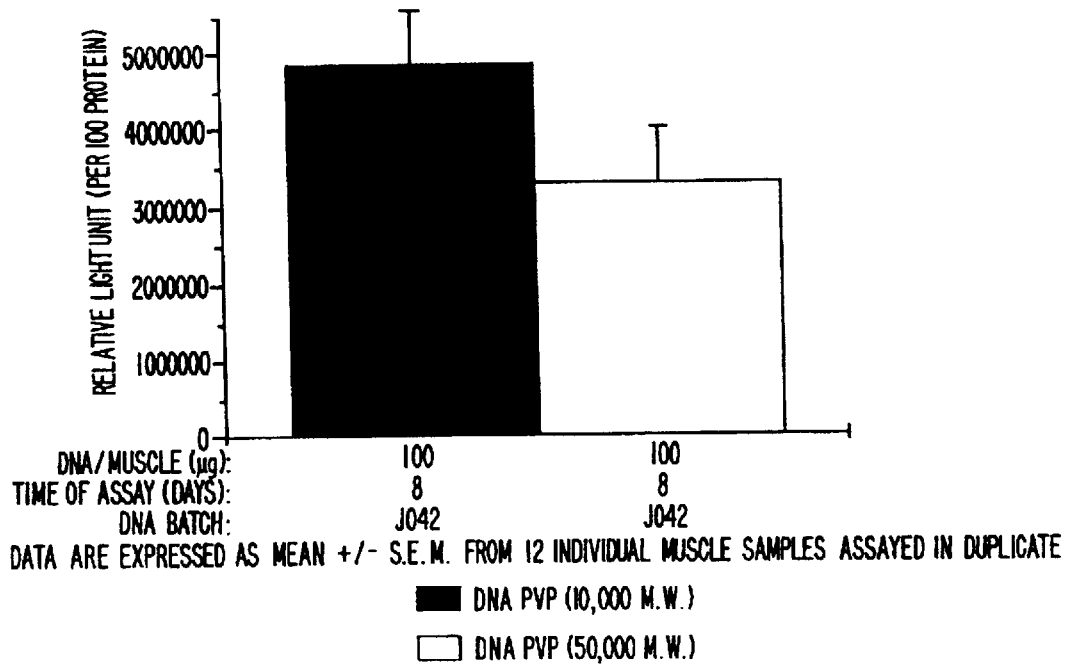
FIG. 6 illustrates that the biologically excretable low molecular weight PVP is equally effective as the high molecular weight species in transfecting muscle tissue.

A liquid scintillation counter may be used as a substitute for a luminometer, however, sensitivity may be lower, Fulton, R., and B. Van Ness, Luminescent Reporter Gene Assays for Luciferase and β-galactosidase Using a Liquid Scintillation Counter, *BioTechniques* 14(5):762–763(1993), incorporated herein by reference and Nguyen, V.T., M. Morange, and 0. Bensaude, Firefly Luciferase Luminescence Assays Using Scintillation Counters for Quantitation in Transfected Mammalian Cells, *Anal. Biochem.* 171:404–408 (1988), incorporated herein by reference. The results are expressed as mean +/−S.E.M of Relative Light Unit, as indicative of β-galactosidase activity, per 100 ug muscle protein. When using a scintillation counter, it is necessary to turn off the coincident circuit in order to measure chemiluminescence directly. The manufacturer of the instrument should be contacted to determine how this is done. If it is not possible to turn off the coincident circuit, a linear relationship can be established by taking the square root of the counts per minute measured and subtracting the instrument background. Actual=(measured-instrument background)$^{1/2}$. Other methods of measuring a chemiluminescent signal as are known in the art may also be utilized. Results: Intramuscular administration of CMV-β-galactosidase expression vector formulated in either saline or 5% PVP (International Specialty Products, Plasdone-C®15, m.w. 10,000 and Plasdone-C®30, m.w. 50,000, Pharmaceutical grade) resulted in the expression of β-galactosidase enzyme in the transfected muscles. The magnitude and time course of β-galactosidase expression was compared between the saline and PVP formulations. As shown in FIG. 4, the magnitude of expression was considerably higher when the DNA was formulated in PVP (50,000 MW) as compared to saline. The enhancement of β-galactosidase expression by PVP over saline was dependent on the dose of DNA injected. At a low DNA dose (12.5 ug/injection) there was no difference in the expression level between PVP and saline formulations. At a higher DNA dose (25–150 ug) the level of expression in PVP was higher compared to saline formulation. The DNA dose response in saline formulation reached a plateau at 25 ug whereas it continued to increase in a linear fashion in PVP formulation in the dose range studied. To further characterize the DNA-PVP formulation, the time course of β-galactosidase expression in PVP was compared with the time course in saline. As shown in FIG. 5, the difference between PVP and saline formulations was maintained throughout the time course. Maximum difference was observed at day 15 after injection. Experiments were also conducted with low molecular weight PVP (10,000 daltons). As shown in FIG. 6, the biologically excretable low molecular weight PVP is equally effective as the high molecular weight species in transfecting muscle tissue. The high and low molecular weight PVP was administered at different concentrations, resulting in solutions with the same viscosity.

EXAMPLE 5

Physical Studies on PVP and PVP-DNA Interactions

PVP-DNA interactions by FTIR: Fourier-Transformed Infra Red (FTIR) has been used to investigate PVP-DNA interactions. From this study, it has been shown that PVP stabilizes the backbone of the DNA, as indicated by the sharpness of bands 970 cm$^{-1}$ and 1086 cm$^{-1}$. The FTIR also suggests a decrease in the resonance character of the bases. There is also a broadening and decrease in intensity from 1400–1600 cm−1 and increased resolution and intensity from 1650–1800 cm$^{-1}$ and 1200–1400 cm$^{-1}$. This is interpreted as a decrease in resonance character associated with the DNA bases when PVP is present. The result is the formation of explicit double and single bond formation. The FTIR (>1650 cm$^{-1}$) also suggests a greater distinction in the environment between exocyclic base residues due to splits in the degeneracy when the PVP is present. Alternatively, the apparent splits may result from the presence of the carbonyl stretching mode associated with PVP.

Mechanism of Action: While the invention is not to be limited by any particular theory, as mechanisms of action, it is postulated that PVP may act as follows:
1. It may protect the DNA by altering the diffusion of nucleases within the polymer matrix. It may also provide water exclusion which may reduce nuclease activity. Consistent with a physical interaction between DNA and PVP, isothermal titration calorimetry measurements using a Hart Scientific microtitration calorimeter gave a positive heat of binding. These measurements indicate a positive enthalpy and suggest that PVP:DNA interactions are driven by the displacement of water or counterions.
2. PVP, through its hydrophobic regions may be capable of interacting, even fusing with biological membranes.
3. When PVP is at the surface of the cell, it will concentrate the associated DNA at that surface. If PVP is also fusogenic, it could then transfer the localized DNA into the cytoplasm.

EXAMPLE 6

Protection of DNA from DNAse I Degradation

Figure 7:
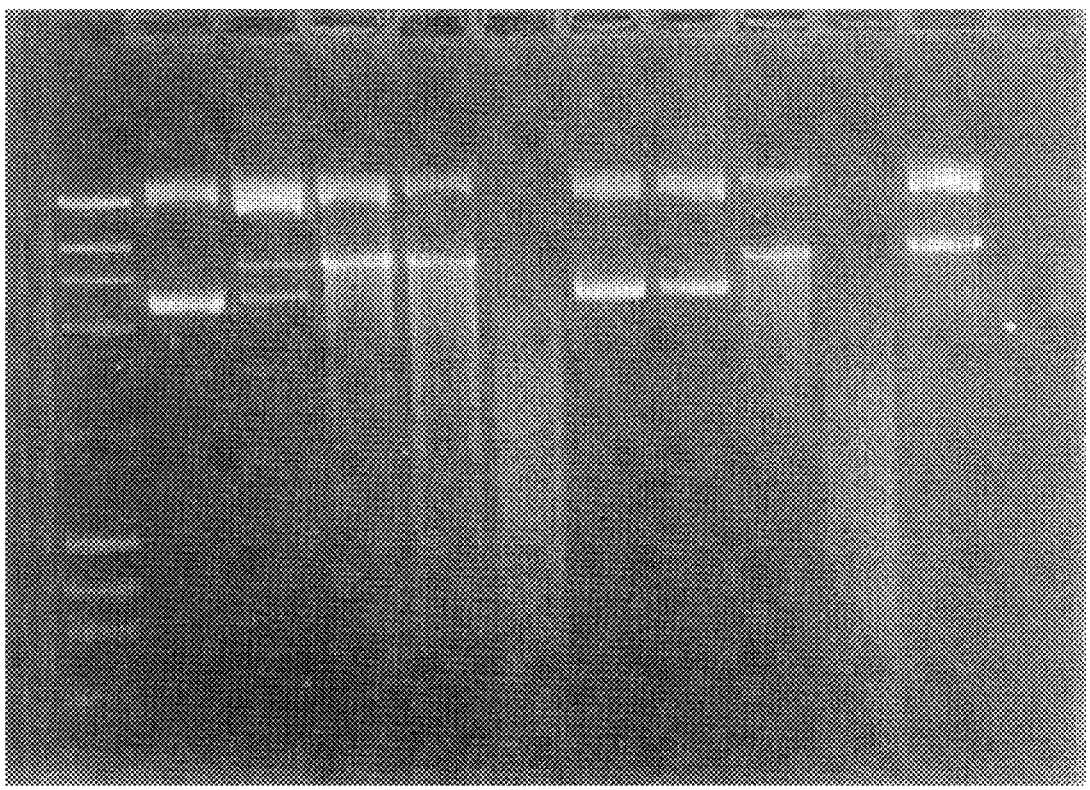
FIG. 7 is an illustration of the results of a gel-electrophoresis undertaken to determine the degree of DNA degraded by DNAse I in saline versus PVP.

Protection of DNA in formulation compositions from DNAse I degradation by 5% PVP was demonstrated. Solutions of DNA alone or DNA in 5% PVP (50 kDa) were prepared at 37° C. in saline DNAse I Activity Buffer (50 mM sodium acetate, pH 6.5 with 10 mM MgCl$_2$, 2 mM CaCl$_2$). The concentration of DNA was 100 ug/ml of Activity Buffer. To all solutions, various amounts of DNAse I in Activity Buffer were added. The weight ratios of DNAse I to DNA were: 1:250,000, 1:50,000, 1:25,000, 1:12,000. The manufacturer of the DNAse I used indicates that 1:10,000 DNAse I to DNA will entirely degrade DNA at 37° C. in 15 minutes. The samples were allowed to incubate at 37° C. for 15 minutes, at which time an aliquot of each sample was added to tracking dye. Gel-electrophoresis was undertaken to quantitate the degree of degraded DNA (FIG. 7). The results showed that higher amounts of DNAse I were needed to degrade DNA in the presence of PVP as compared to the absence of PVP. These results have been confirmed in other tests, demonstrating that the PINCs (e.g., PVP) reduce the rate of nuclease digestion of the nucleic acid molecules in the compositions of this invention.

EXAMPLE 7

Figure 8:
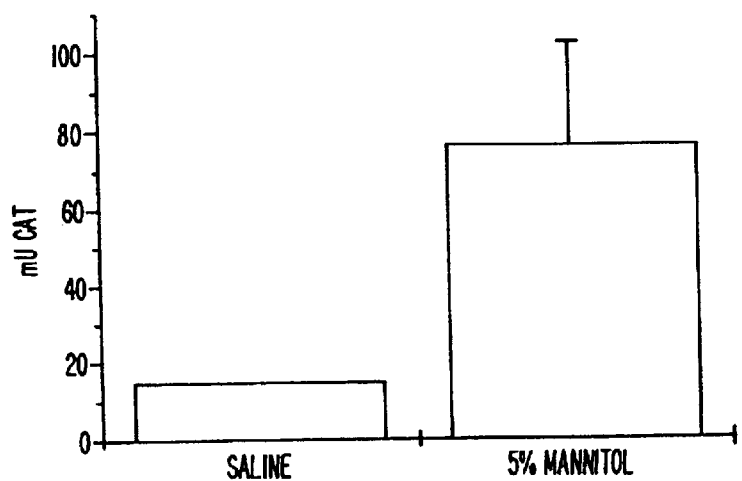
FIG. 8 is an illustration of the effect of administering DNA containing a CAT reporter gene in 5% mannitol versus saline.

Increase in Expression of a Reporter Gene Administered in Mannitol Versus Saline As shown in FIG. 8, the effect of administering DNA containing a chloramphenicol acetyltransferase (CAT) reporter gene in 5% mannitol versus saline was investigated. The use of CAT as a reporter gene is well known in the art. A typical protocol may be found in Current Protocols in Molecular Biology, Chapter 9, Unit 9.6A Reporter System Using Chloramphenicol Acetyltransferase© 1993 Current Protocols. As shown in FIG. 8, the expression of the CAT reporter gene in 5% mannitol was approximately four times that when administered in saline. The DNA was administered to the tibialis muscle of rats as described above in Example 4.

EXAMPLE 8

Increase in Expression of a Reporter Gene Administered in PVA Versus Saline

Figure 9:
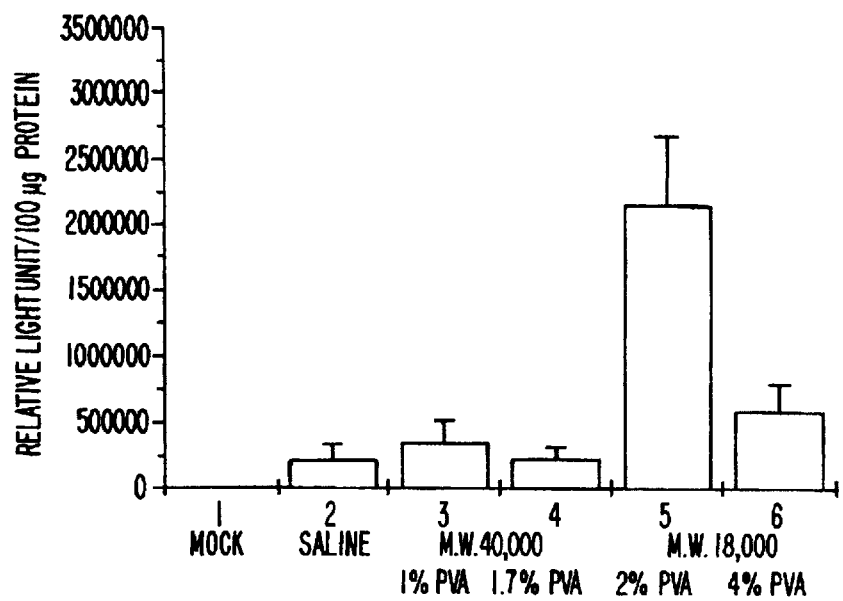
FIG. 9 is an illustration of the effect of administering PVA containing a CMV-β-galactosidase reporter gene in high molecular weight (40,000 daltons) at 1% PVA or 1.7% PVA and low molecular weight (18,000 daltons) at 2% PVA or 4% PVA.

As shown in FIG. 9, the effect of administering DNA containing a CMV-β-galactosidase reporter gene in high molecular weight PVA (40,000 daltons) at 1% PVA or 1.7% PVA and low molecular weight PVA (18,000 daltons) at 2% PVA or 4% PVA was investigated. The low molecular weight PVA at both 2% and 4% gave approximately two and six times expression, respectively, of the reporter gene as saline. Determination of the level of expression of the reporter gene was performed as described above in Example 4. The DNA was administered to the tibialis muscle of rats as described above in Example 4.

EXAMPLE 9

Increase in Expression of a Reporter Gene Administered in Propylene Glycol versus Saline The effect of administering DNA in 10.8% propylene glycol versus saline was also investigated. The expression of the CMV-β-galactosidase reporter gene in 10.8% propylene glycol was found to be approximately three times that when administered in saline. Determination of the level of expression of the reporter gene was performed as described above in Example 4. The DNA was administered to the tibialis muscle of rats as described above in Example 4.

EXAMPLE 10

Effect of Methylated Monomeric PVP on Expression

Figure 10:
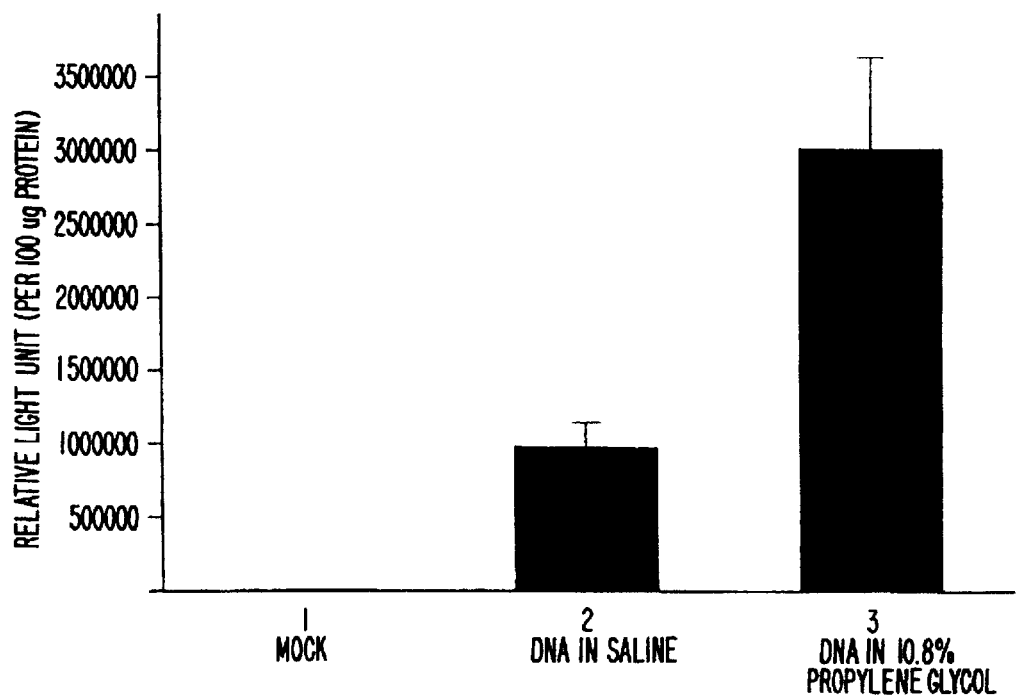
FIG. 10 is a bar graph showing the relative expression levels for a β-gal plasmid in rat tibialis muscle for formulations containing 5% PVP as compared to formulations containing 5, 25, and 50% NM2P.

The effect of a non-polymeric PINC system was also examined, using N-methyl-2-pyrrolidone (NM2P). NM2P is a methylated monomer of PVP. NM2P has been used to increase the aqueous solubility of hydorphobic drugs and to enhance the topical and transdermal permeation of drugs. The enhanced solubility of drug molecules by NM2P has been attributed to complexation between the amide groups of NM2P and certain drugs due to hydrogen bonding. NM2P, like PVP, is a strong hydrogen bond acceptor. The expression of β-galactosidase in muscle from CMV-β-gal plasmid formulated with different concentrations of NM2P and 5% PVP were compared. A 5% NM2P formulation resulted in approximately 2-fold higher levels of β-galactosidase expression in rat tibialis muscle at 7 days as compared to the 5% PVP formulation (FIG. 10). Gel electrophoresis results demonstrated that the CMV-β-gal plamid formulated in NM2P at concentrations up to 80% was stable as determined by retained supercoiled plasmid. These results indicate that the PINC formulations can include non-polymeric amphiphilic compounds.

EXAMPLE 11

Expression of PINC Formulation in Tumors

In addition to the enhanced expression observed for DNA/PINC formulations in muscle tissue, the expression of a reporter gene (CAT) in mouse solid tumors was evaluated for formulations incorporating CMV-gal with one of saline, DOTMA/chol, or a PINC. CMV-CAT was complexed with different amounts of five prototype PINC systems, saline, and in a cationic lipid complex. With all formulations except the cationic lipid complex, the dose of plasmid injected into the tumors was 140 µg. The dose injected with the cationic lipid complex was 20 µg. 50 µL of each formulation was injected into the tumor. CAT expression was determined 24 hours post-administration using a CAT ELISA.

The five PINC systems were selected due to previous results found after intramuscular injection of reporter genes (as described above). These five formulations were found to result in the largest increase in the levels of gene expression over saline in muscle of those tested.

The enhancement of CAT expression with the five prototype PINC systems (including 4% PVA) was 3–13 fold over saline and 40–146 fold over the cationic lipid complex. The enhancement of CAT expression with the PINC systems over the cationic lipid complex when normalized to the dose injected was 6–21 fold. These results confirm that the PINC systems perform similarly in two types of solid tissues, muscle and tumor. The results are shown graphically in FIG. 11.

EXAMPLE 12

Specific Applications of PINC Systems

A. Muscle-specific Human IGF-I/PVP

Insulin-like growth factor (IGF-I) has been shown to have a vital role in the growth and regeneration of peripheral nerves and skeletal muscle [Ishii, D. N., et al., 1985, *Int. J. Neurosci*. 26:109–127; Neff, N. T., et al., 1993, *J. Neurobiology*. 24:1578–1588; Sjoberg, J., and Kanje, M., 1989, *Brain Res*. 485:102–108; Caroni, P., and Grandes, P., 1990, *J. Cell. Biol*. 110:1307–1317]. Previous studies have demonstrated that the administration of recombinant IGF-I (rIGF-I) to animals has therapeutic effects in models of neuromuscular disease and injury. Systemic administration of rIGF-I to humans has potential for treating neuromuscular conditions. However, the need for frequent dosing and the potential for systemic toxicities limit its therapeutic applications. To overcome these potential problems, we have developed a muscle-specific IGF-I gene medicine for local effects after intramuscular injection. A muscle-specific IGF-I expression plasmid was constructed by linking the promoter/enhancer regions of a avian skeletal α-actin gene to the IGF-I gene [Coleman, M. E., et al., 1997, Submitted to *American J. Phys*.; Alila, H., et al., 1997. Submitted to *Hum. Gene Therapy*].

A muscle-specific IGF-I expression plasmid, complexed to PVP (1:17 w/w) and formulated in 150 mM NaCl, resulted in an enhancement IGF-I expression of approximately 200-fold in mouse quadricep muscle at 7 days as compared to the same plasmid formulated in saline.

We have determined the effects of the IGF-I gene medicine on indices of nerve regeneration in mice following sciatic nerve crush [Rabinovsky, E., et al., 1997. Submitted to *Nature Medicine*]. Mice were subjected to unilateral sciatic nerve crush immediately distal to the sciatic notch. IGF-I gene medicine or control plasmid were injected into the tibialis anterior muscle (75 µg) and the gastrocnemius (150 µg) muscle at day 7, 14, 21, and 28 days post nerve crush. Sciatic nerve conduction velocity and wave amplitude were determined at 14, 21, 28, and 56 day post nerve crush. The results indicate that the IGF-I gene medicine can provide an improvement in both sciatic nerve conduction velocity and wave amplitude ($p<0.01$).

We have also determined that the IGF-I gene medicine can reduce atrophy and loss of muscle strength in a hindlimb suspension mouse model [Coleman, M. E., et al. 1997. Submitted to *American J. Phys*.]. Mice were subjected to 14 days of hindlimb suspension [Haida, N., et al., 1989, *Exper. Neuro*. 103:68–76] and injected with the IGF-I gene medicine at days 0 and 7 of the suspension phase. Contractile force measurements and muscle weights determined 1–2 days after cessation of hindlimb suspension showed that treatment with the IGF-I gene medicine reduced muscle atrophy (p<0.05) and loss of contractile force caused by hindlimb suspension.

B. Muscle-specific Human Growth Hormone/PVP

A muscle-specific growth hormone expression plasmid (pSK-hGH) was complexed to PVP (1:17 w/w) and formulated in 150 mM NaCl. The growth hormone gene medicine was tested for in vivo expression and efficacy in hypophysectomized rats [Anwer, K. Shi, et al., 1997. Submitted to *Nature Medicine*]. A single intramuscular injection of the complex formulated in 150 mM NaCl to growth hormone deficient rats resulted in a statistically significant increase in the growth rate of rats over 21 days as compared to rats injected with a control plasmid. The average daily weight gain increased over 21 days from 0.29±0.09 g to 0.61±0.08 g (p<0.05). The increase in growth rate observed from the injection of pSK-hGH plasmid resulted in an increase in rat IGF-I levels in blood from 34.7±7.25 ng/mL to 145.4±77 ng/mL 21 days after injection (p<0.05). No hGH was detected in the blood of rats. This was most likely due to i) low bioavailability and short half-life of hGH in blood and/or ii) production of anti-hGH antibodies in rat which would make detection of hGH in blood more difficult. In other studies, we have detected surrogate protein having a longer half-life than hGH in the blood after the intramuscular administration of a similar muscle-specific gene medicine [Anwer, K. Shi, et al.,1997. Submitted to *Nature Medicine*].

The references cited herein are hereby incorporated by reference to the same extent as if each had been individually stated to be so incorporated.

The invention illustratively described herein suitably may be practiced in the absence of any element or elements, limitation or limitations which is not specifically disclosed herein. Thus, in particular embodiments, the term "comprising" may be replaced by "consisting essentially of". Further, it will be readily apparent to one skilled in the art that various substitutions and modifications may be made to the invention disclosed herein without departing from the scope and spirit of the invention. Other embodiments are within the following claims.

What is claimed is:

1. A method of administering to a mammal a composition for delivery of a nucleic acid molecule to a cell, comprising the step of
    introducing said composition into a tissue of a mammal,
    wherein said composition comprises polyvinyl pyrrolidone and said nucleic acid molecule,
    wherein said polyvinyl pyrrolidone directly interacts with and enhances the delivery of said nucleic acid to mammalian cells in vivo.

2. The method of claim 1, wherein said nucleic acid molecule is a deoxyribonucleic acid molecule.

3. The method of claim 1, wherein said nucleic acid molecule encodes a polypeptide or protein.

4. The method of claim 1, wherein said step of introducing said composition into a tissue of a mammal is by injection.

5. The method of claim 1, wherein said tissue is muscle.

6. The method of claim 1, wherein said tissue is a tumor.

7. The method of claim 1, wherein said composition further comprises a targeting ligand.

8. The method of claim 1, wherein the tissue is an interstitial joint space.

9. A method of administering to a mammal a composition for delivery of a nucleic acid molecule to a cell, comprising the step of
    introducing said composition into the interstitial joint space of a mammal,
    wherein said composition comprises polyvinyl pyrrolidone and said nucleic acid molecule,
    wherein said polyvinyl pyrrolidone directly interacts with and enhances the delivery of said nucleic acid to mammalian cells in vivo.

10. The method of claim 9, wherein said composition further comprises a targeting ligand.

11. The method of claims 1 or 9, wherein said composition consists essentially of said polyvinyl pyrrolidone and said nucleic acid molecule.

12. A method of administering to a mammal a composition for delivery of a nucleic acid molecule to a cell, comprising the step of:
    introducing said composition into a muscle and/or tumor tissue of a mammal in vivo, wherein said composition comprises said nucleic acid molecule formulated with a compound that directly interacts with and is non-condensing with respect to the nucleic acid, wherein the compound is selected from the group consisting of: polyvinyl pyrrolidone, polyvinyl alcohol, polyethylene glycol, polypropylene glycol, poloxamer 407, n-methyl-2-pyrrolidone, and co-polymers thereof.

13. The method of claim 12, wherein the compound is present in an amount that is insufficient for gel formation.

14. The method of claim 12, wherein said nucleic acid molecule is a deoxyribonucleic acid molecule.

15. The method of claim 12, wherein said nucleic acid molecule encodes a polypeptide or protein.

16. The method of claim 12, wherein said step of introducing said composition into a tissue of a mammal is by injection.

17. The method of claim 16, wherein said tissue is muscle.

18. The method of claim 16, wherein said tissue is a tumor.

19. The method of claim 12, wherein said compound is polyvinyl pyrrolidone.

20. The method of claim 12, wherein said composition further comprises a targeting ligand.

* * * * *